United States Patent
Zimmerman et al.

(10) Patent No.: US 9,938,516 B2
(45) Date of Patent: Apr. 10, 2018

(54) NON-NATURAL AMINO ACID TRNA SYNTHETASES FOR PARA-METHYLAZIDO-L-PHENYLALANINE

(71) Applicant: SUTRO BIOPHARMA, INC., South San Francisco, CA (US)

(72) Inventors: Erik S. Zimmerman, Pacifica, CA (US); Christopher Thanos, Tiburon, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 52 days.

(21) Appl. No.: 15/028,396

(22) PCT Filed: Oct. 10, 2014

(86) PCT No.: PCT/US2014/060058
§ 371 (c)(1),
(2) Date: Apr. 8, 2016

(87) PCT Pub. No.: WO2015/054587
PCT Pub. Date: Apr. 16, 2015

(65) Prior Publication Data
US 2016/0257946 A1    Sep. 8, 2016

Related U.S. Application Data

(60) Provisional application No. 61/890,028, filed on Oct. 11, 2013.

(51) Int. Cl.
| | |
|---|---|
| *C12N 9/00* | (2006.01) |
| *C07K 1/02* | (2006.01) |
| *C12P 21/02* | (2006.01) |
| *A61K 31/40* | (2006.01) |
| *A61K 47/48* | (2006.01) |
| *C07K 16/32* | (2006.01) |

(52) U.S. Cl.
CPC ............... *C12N 9/93* (2013.01); *A61K 31/40* (2013.01); *A61K 47/48384* (2013.01); *A61K 47/48584* (2013.01); *C07K 1/02* (2013.01); *C07K 16/32* (2013.01); *C12P 21/02* (2013.01); *C12Y 601/01* (2013.01); *C12Y 601/01001* (2013.01)

(58) Field of Classification Search
CPC .. A61K 38/00; A61K 47/48438; C07K 16/30; C12Y 601/01; C12Y 601/01001
See application file for complete search history.

(56) References Cited

U.S. PATENT DOCUMENTS

2008/0233611 A1    9/2008  Schultz et al.

OTHER PUBLICATIONS

Christopher G. Bazewicz, Sensitive, Site-Specific, and Stable Vibrational Probe of Local Protein Environments: 4-Azidomethyl-L-Phenylalanine J. Phys. Chem. B 2013, 117, 8987-8993.*
Bazewicz, et al., "Sensitive, Site-Specific, and Stable Vibrational Probe of Local Protein Environments: 4-Azidomethyl-L-Phenylalanine", J. Phys. Chem. B, 117(30), Aug. 1, 2013, pp. 8987-8993.
PCT/US2014/060058, , "International Search Report and Written Opinion", dated Jan. 22, 2015, 8 pages.
EP14852519.9, "Extended European Search Report", dated Feb. 16, 2017, 6 pages.
PCT/US2014/060058, "International Preliminary Report on Patentability", dated Apr. 21, 2016, 13 pages.
Zimmerman et al., "Production of Site-Specific Antibody-Drug Conjugates Using Optimized Non-Natural Amino Acids in a Cell-Free Expression System", Bioconjugate Chemistry, vol. 25, issue No. 2, Jan. 17, 2014, pp. 351-361.

* cited by examiner

*Primary Examiner* — Kagnew H Gebreyesus
(74) *Attorney, Agent, or Firm* — Kilpatrick Townsend & Stockton LLP

(57) ABSTRACT

The invention provides methods and compositions for a mutein aminoacyl-tRNA synthetase that preferentially charges a tRNA with a non-natural amino acid. Also provided are methods for incorporating the non-natural amino acid, para-methylazido-L-phenylalanine into a protein and further conjugating a biologically active adduct to the para-methylazido-L-phenylalanine.

22 Claims, 3 Drawing Sheets

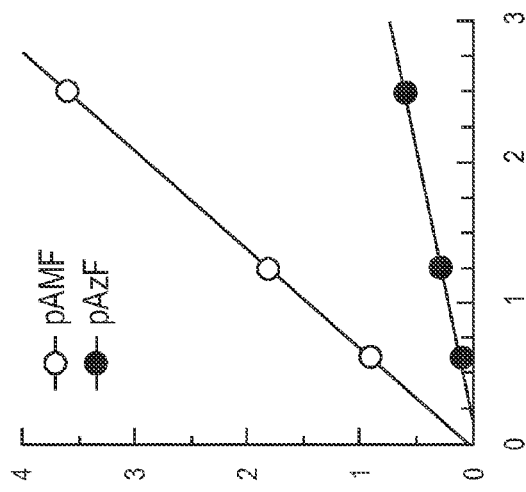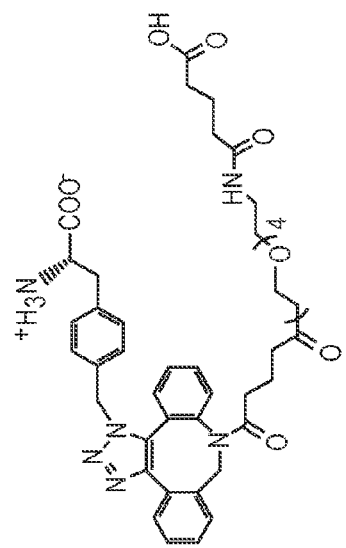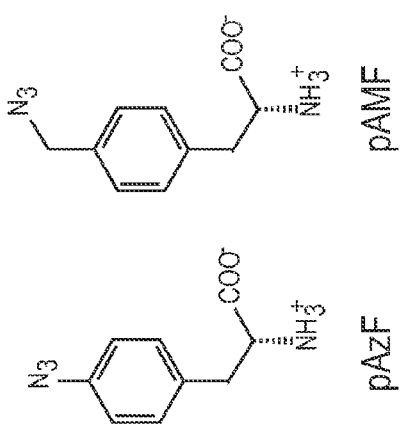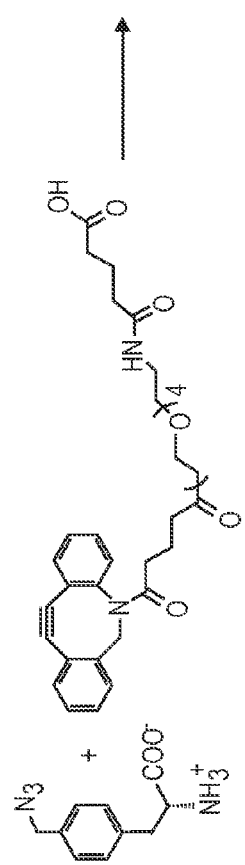
FIG. 2A
FIG. 2B
FIG. 2C

| pAMFRS variant | 32 | 65 | 108 | 109 | 158 | 159 | IgG HC 136-AB3627 DAR | EC50 (nM) |
|---|---|---|---|---|---|---|---|---|
| A01 | T | A | Y | L | A | S | 1.48 | 0.071 |
| A04 | V | A | W | M | A | G | 1.68 | 0.047 |
| B03 | A | V | W | Q | A | G | 1.70 | 0.043 |
| C10 | V | V | Y | Q | A | V | 1.68 | 0.048 |
| D08 | T | V | W | Q | A | S | 1.68 | 0.044 |
| C02 | V | V | W | I | A | S | 1.64 | 0.044 |

# NON-NATURAL AMINO ACID TRNA SYNTHETASES FOR PARA-METHYLAZIDO-L-PHENYLALANINE

CROSS-REFERENCES TO RELATED APPLICATIONS

This application is a U.S. National Phase under 35 USC 371 of PCT Application No. PCT/US2014/060058, filed Oct. 10, 2014, which claims priority to U.S. Provisional Application No. 61/890,028, filed Oct. 11, 2013, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named "Sequence Listing for 091200-1007297-006110US.txt" created Sep. 26, 2014, and containing 11,414 bytes. The material contained in this text file is incorporated by reference in its entirety for all purposes.

BACKGROUND OF THE INVENTION

Protein drug conjugates such as antibody drug conjugates (ADCs) are a targeted chemotherapeutic currently at the cutting edge of oncology medicine. ADCs, for example, consist of a tumor antigen-specific antibody that is coupled to a chemotherapeutic small molecule cytotoxin. Through targeted delivery of potent cytotoxins, protein drug conjugates exhibit improved therapeutic index over traditional chemotherapies with enhanced efficacy relative to standard monoclonal antibody therapies. However, current methods utilize nonspecific modes of conjugation of drugs to proteins, thereby leading to heterogeneous drug products with varied numbers of drugs conjugated across a number of possible sites. Technical challenges associated with drug conjugation to proteins using naturally occurring amino acids, are primarily due to heterogeneous degrees and location of drug loading as well as conjugate instability.

In order to reduce product heterogeneity, several groups have reported site-directed approaches that utilize substituted cysteines or enzymatic modification of engineered glutamine for conjugation. Site-specific ADCs have comparable potency to randomly conjugated ADCs while exhibiting superior therapeutic index and pharmacokinetics. However, limitations exist in thiol-based coupling stability due to plasma hydrolysis of the succinimide ring of the thiomaleimide conjugate, resulting in drug transfer to serum albumin. Furthermore, the partial reduction and reformation of disulfide bonds that facilitates conjugation to the engineered free cysteine, can lead to aberrant disulfide-mediated quaternary structure. An alternative to using introduced free cysteine residues is to use site-specific incorporation of non-natural amino acids with chemical side chains that are compatible with bio-orthogonal conjugation chemistry.

The essential componentry of any non-natural amino acid (nnAA) incorporation system consists of an aminoacyl tRNA synthetase (aaRS) that charges a specific tRNA with a nnAA. The aaRS-tRNA pair must be orthogonal with respect to the host cell or expression system in which they are employed. That is, the nnAA-specific synthetase must not recognize any host tRNAs or cognate amino acids, and the tRNA must not be aminoacylated by any host aaRS. Additionally, the orthogonal tRNA anticodon is often mutated to recognize a stop or nonsense codon. Repurposing of non-proteinogenic codons, such as the amber stop codon TAG, enables incorporation of a nnAA at any site in a protein through mutagenesis of the mRNA coding sequence to TAG. Amber suppression is the most widely used mode of co-translational, enzyme catalyzed nnAA incorporation. Non-natural amino acids with bio-orthogonal reactive chemical side chains can be used as a chemical "handle" to conjugate various payloads to discrete sites in a protein. This approach can generate additional functionality to proteins by direct conjugation of biologically active adduct, such as fluorescent or radioactive labels, photoactivatable markers, pharmacokinetic modifying PEGs, or chemotherapeutic agents. Unfortunately, the current methods for nnAA incorporation and conjugation of bio-orthogonal reactive chemical side chains into proteins are hindered by low overall product yield, nnAA incorporation inefficiency and low conjugation efficiency.

There is a need in the art for improved methods of site-specific incorporation of nnAAs and conjugation of biologically active adducts to proteins to form homogeneously conjugated protein drug conjugate therapeutics. The present invention satisfies these and other needs.

BRIEF SUMMARY OF THE INVENTION

In a first aspect, the present invention provides a composition comprising an aminoacyl-tRNA synthetase (RS) wherein the RS:
  i) preferentially aminoacylates to a degree of greater than 90% a tRNA with para-methylazido-L-phenylalanine (pAMF) compared to the 20 common naturally occurring amino acids;
  ii) has a sequence identity of over 80% to *Methanococcus jannaschii* tyrosyl tRNA synthetase (TyrRS) having SEQ ID NO:1; and
  iii) using SEQ ID NO: 1 as a reference sequence, has:
    a) at position 65 amino acid: A or V;
    b) at position 108 amino acid: Y or W;
    c) at position 158 amino acid: A;
    d) at position 32 amino acid: T or V or A; and
    e) at position 159 amino acid: S or G or V.

The composition of the RS variant can have amino acid substitutions at amino acid position 65 for A or V (e.g., L65A or L65V), at amino acid position 108 for Y or W (e.g., F108Y or F108W), at amino acid position 158 for A (e.g., D158A); at amino acid position 32 for T or V or A (e.g., Y32T or Y32V or Y32A); and at amino acid position 159 for S or G or V (e.g., I159S or I159G or I159V). In some embodiments, the composition further includes an amino acid substitution at position Q109 selected from the group of amino acids consisting of L or M or I (e.g., Q109L, Q109M or Q109I).

In some embodiments, the RS has a sequence identity of over 80%, e.g., 81%, 82%, 83%, 84%, 85%, 86%, 87%, 88%, 89%, 90%, 91%, 92%, 92%, 93%, 94%, 95%, 96%, 97%, 98%, 99% or 100% of SEQ ID NO: 1. In some embodiments, the RS has a sequence identity of at least 90% of SEQ ID NO: 1 and has amino acid substitutions selected from the group consisting of: 1) Y32T, L65A, F108Y, Q109L and I159S; ii) Y32V, L65A, F108W, Q109M and I159G; iii) Y32A, L65V, F108W and I159G; iv) Y32V, L65V, F108Y and I159V; v) Y32T, L65V, F108W and I159S; and vi) Y32V, L65V, F108W, G109I and I159S. In another embodiment, the RS is selected from the group of amino acid sequences consisting of SEQ ID NO: 2 and SEQ ID NO: 3. The RS can have an amino acid sequence identity of over 80%, e.g., 80%, 81%, 82%, 83%, 84%, 85%, 86%, 87%, 88%, 89%, 90%, 91%, 92%, 93%, 94%, 95%, 96%, 97%, 98%, 99% or 100% identity, to the wild-type *Methanococcus jannaschii* tyrosyl tRNA synthetase (TyrRS) sequence (SEQ ID NO: 1). The RS can have an amino acid sequence identity of at least 90% of SEQ ID NO: 1, e.g., 90%, 91%, 92%, 93%, 94%, 95%, 96%, 97%, 98%, 99% or 100% sequence identity to SEQ ID NO: 1.

In a second aspect, the present invention provides is a polynucleotide encoding an aminoacyl-tRNA synthetase (RS) wherein the RS:
  i) preferentially aminoacylates to a degree of greater than 90% a tRNA with para-methylazido-L-phenylalanine (pAMF) compared to the 20 common naturally occurring amino acids;
  ii) has a sequence identity of over 80% to *Methanococcus jannaschii* tyrosyl tRNA synthetase (TyrRS) having SEQ ID NO: 1; and
  iii) using SEQ ID NO: 1 as a reference sequence, has:
    a) at position 65 amino acid: A or V;
    b) at position 108 amino acid: Y or W;
    c) at position 158 amino acid: A;
    d) at position 32 amino acid: T or V or A; and
    e) at position 159 amino acid: S or G or V.

In some embodiments, the polynucleotide further has an amino acid substitution at position Q109 selected from the group of amino acids consisting of L or M or I (e.g., Q109L, Q109M or Q109I).

In some embodiments, the RS has a sequence identity of at least 90% of SEQ ID NO:1 and has amino acid substitutions selected from the group consisting of: 1) Y32T, L65A, F108Y, Q109L and I159S; ii) Y32V, L65A, F108W, Q109M and I159G; iii) Y32A, L65V, F108W and I159G; iv) Y32V, L65V, F108Y and I159V; v) Y32T, L65V, F108W and I159S; and vi) Y32V, L65V, F108W, G109I and I159S. In one embodiment, the RS is selected from the group of amino acid sequences consisting of SEQ ID NO: 2 and SEQ ID NO: 3.

In a third aspect, the present invention provides is a cell free protein synthesis system for selectively incorporating para-methylazido-L-phenylalanine (pAMF) into a protein of interest, the system comprising:
  a) a cell free extract of bacteria having biologically functioning tRNA, amino acids and ribosomes necessary for cell free protein synthesis;
  b) a polynucleotide having a coding region encoding the protein of interest and including a suppression codon selectively positioned within its coding region;
  c) methylazido-L-phenylalanine in a concentration sufficient to permit selective incorporation of pAMF into the protein of interest;
  d) a tRNA able to be charged with pAMF and complementary to the suppression codon of the protein of interest; and
  e) an aminoacyl-tRNA synthetase (RS) wherein the RS:
    i) preferentially aminoacylates to a degree of greater than 90% a tRNA with para-methylazido-L-phenylalanine (pAMF) compared to the 20 common naturally occurring amino acids;
    ii) has a sequence identity of over 80% to *Methanococcus jannaschii* tyrosyl tRNA synthetase (TyrRS) having SEQ ID NO:1; and
    iii) using SEQ ID NO:1 as a reference sequence, has:
      a) at position 65 amino acid: A or V; b) at position 108 amino acid: Y or W; c) at position 158 amino acid: A; d) at position 32 amino acid: T or V or A; and e) at position 159 amino acid: S or G or V.

In some embodiments, the cell free protein synthesis system further has an amino acid substitution at position Q109 selected from the group of amino acids consisting of L or M or I.

In some embodiments, the RS has a sequence identity of over 80%, e.g., 81%, 82%, 83%, 84%, 85%, 86%, 87%, 88%, 89%, 90%, 91%, 92%, 92%, 93%, 94%, 95%, 96%, 97%, 98%, 99% or 100% of SEQ ID NO: 1. In some embodiments, the RS has a sequence identity of at least 90% of SEQ ID NO: 1 and comprises amino acid substitutions selected from the group consisting of: i) Y32T, L65A, F108Y, Q109L and I159S; ii) Y32V, L65A, F108W, Q109M and I159G; iii) Y32A, L65V, F108W and I159G; iv) Y32V, L65V, F108Y and I159V; v) Y32T, L65V, F108W and I159S; and vi) Y32V, L65V, F108W, G109I and I159S. In one embodiment, the RS is selected from the group of amino acid sequences consisting of SEQ ID NO: 2 and SEQ ID NO: 3.

In some embodiments, the cell free extract has an active oxidative phosphorylation system. In some embodiments, the protein of interest is an antibody or antibody fragment.

In a fourth aspect, the present invention provides is a method for selectively incorporating para-methylazido-L-phenylalanine (pAMF) into a protein of interest, the method comprising the steps of:
  a) combining a cell free extract of bacteria having containing biologically functioning tRNA, amino acids and ribosomes necessary for cell free protein synthesis with the following reagents:
    i) a polynucleotide having a coding region encoding the protein of interest and including a suppression codon selectively positioned within its coding region;
    ii) methylazido-L-phenylalanine in a concentration sufficient to permit selective incorporation of pAMF into the protein of interest;
    iii) a tRNA able to be charged with pAMF and complementary to the suppression codon of the protein of interest; and
    iv) an aminoacyl-tRNA synthetase (RS) wherein the RS: preferentially aminoacylates to a degree of greater than 90%, a tRNA with para-methylazido-L-phenylalanine (pAMF) compared to the 20 common naturally occurring amino acids; has a sequence identity of over 80% to *Methanococcus jannaschii* tyrosyl tRNA synthetase (TyrRS) having SEQ ID NO: 1 (WT); and using SEQ ID NO:1 as a reference sequence, has: 1) at position 65 amino acid: A or V; 2) at position 108 amino acid: Y or W; 3) at position 158 amino acid: A; 4) at position 32 amino acid: T or V or A; and 5) at position 159 amino acid: S or G or V; and
  b) incubating the combination of step (a) under conditions permitting selective incorporation of pAMF into the protein of interest.

In some embodiments, the method further has an amino acid substitution at position Q109 selected from the group of amino acids consisting of L or M or I.

In some embodiments, the RS has a sequence identity of over 80%, e.g., 81%, 82%, 83%, 84%, 85%, 86%, 87%, 88%, 89%, 90%, 91%, 92%, 92%, 93%, 94%, 95%, 96%, 97%, 98%, 99% or 100% of SEQ ID NO: 1. In some embodiments, the RS has a sequence identity of at least 90% of SEQ ID NO: 1 and has amino acid substitutions selected from the group consisting of: 1) Y32T, L65A, F108Y, Q109L and I159S; ii) Y32V, L65A, F108W, Q109M and I159G; iii) Y32A, L65V, F108W and I159G; iv) Y32V, L65V, F108Y and I159V; v) Y32T, L65V, F108W and I159S; and vi) Y32V, L65V, F108W, G109I and I159S. In one embodiment, the RS is selected from the group of amino acid sequences consisting of SEQ ID NO: 2 and SEQ ID NO: 3.

In some embodiments, the cell free extract has an active oxidative phosphorylation system. In some embodiments, the protein of interest is an antibody or antibody fragment.

In some embodiments, the method further comprise the step of conjugating a biologically active adduct to the pAMF of the protein of interest. In some instances, the conjugation is by a 1,3-cycloaddition of an azide with a strained alkyne.

Other objects, features, and advantages of the present invention will be apparent to one of skill in the art from the following detailed description and figures.

BRIEF DESCRIPTION OF THE DRAWINGS

FIGS. 2A-C show the copper-free click conjugation kinetics. FIG. 2A shows the chemical structure of para-azido-L-phenylalanine (left) and para-azidomethyl-L-phenylalanine (right). FIG. 2B shows the kinetics of the formation of the conjugated product. FIG. 2C shows the copper-free click reaction.

FIG. 3A shows that trastuzumab ADCs (trastuzumab-HC136-MMAF) generated with pAMF-specific RS variants have high DAR values. FIG. 3B shows the cytotoxic activity for different trastuzumab ADCs generated using a particular RS variant.

DETAILED DESCRIPTION OF THE INVENTION

Figure 1:
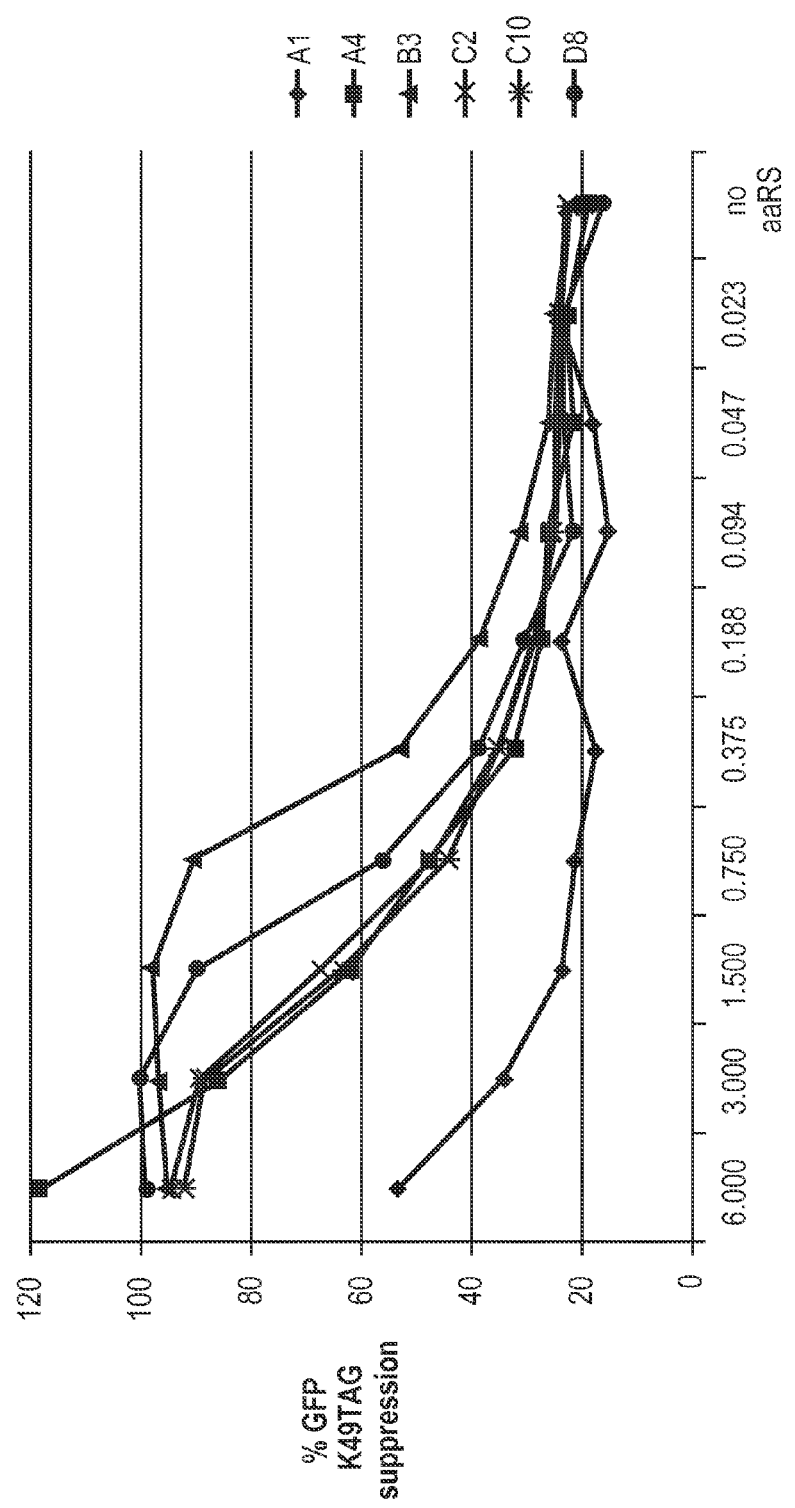
FIG. 1 shows the percentage of GFP expression compared to the level of RS protein used in the GFP K49TAG amber suppression assay for the A01, A04, B03, C02, C10 and D08 muteins. The amino acid substitutions relative to wild-type *M. jannaschii* TyrRS for each of the muteins is presented in FIG. 3A.
Figures 3A, 3B:
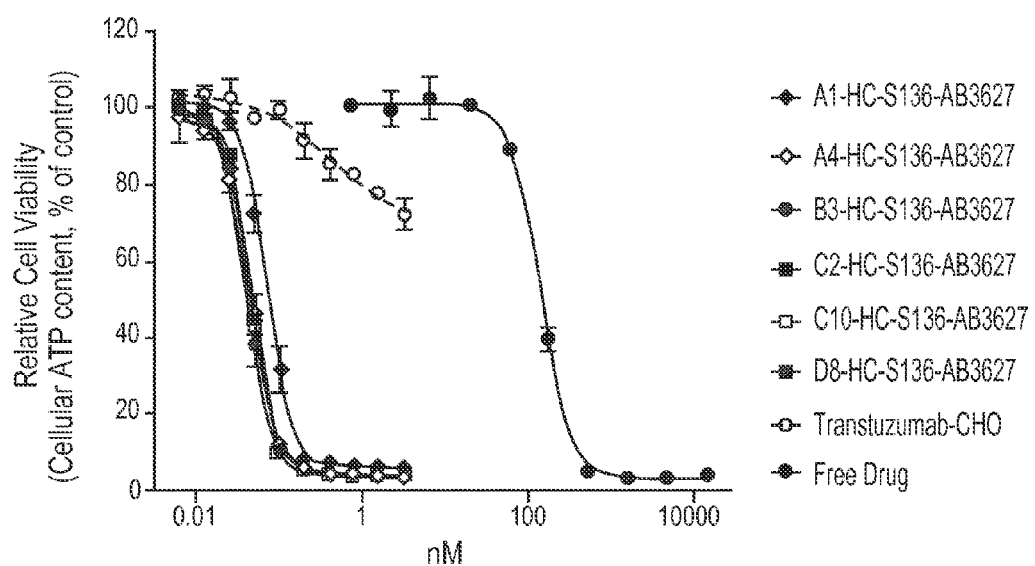
FIGS. 3A-B show that pAMF-specific RS variants were used to produce potent antibody-drug conjugates.

Provided herein are compositions and methods for the site-specific incorporation of the non-natural amino acid para-methylazido-L-phenylalanine (pAMF) into proteins of interest using a cell-free synthesis system. In addition, provided herein is a composition of a variant of the *Methanococcus jannaschii* tyrosyl tRNA synthetase (TyrRS) having high activity and increased specificity for pAMF compared to the common naturally occurring amino acids.

I. DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989); Ausubel et al., CURRENT PROTOCOLS IN MOLECULAR BIOLOGY, John Wiley and Sons (Hoboken, N.Y. 1995).

As used herein the singular forms "a," "and," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The term "aminoacylation" or "aminoacylate" refers to the complete process in which a tRNA is charged with its correct amino acid that is a result of adding an aminoacyl group to a compound. As it pertains to this invention, a tRNA that undergoes aminoacylation or has been aminoacylated is one that has been charged with an amino acid, and an amino acid that undergoes aminoacylation or has been aminoacylated is one that has been charged to a tRNA molecule.

The term "aminoacyl-tRNA synthetase" or "tRNA synthetase" or "synthetase" or "aaRS" or "RS" refers to an enzyme that catalyzes a covalent linkage between an amino acid and a tRNA molecule. This results in an aminoacylated tRNA molecule, which is a tRNA molecule that has its respective amino acid attached via an ester bond.

The term "charged" in the context of tRNA refers to a the aminoacylation of a tRNA with an amino acid, both natural and non-natural, where the aminoacylation permits a ribosome to incorporate the amino acid into a polypeptide being translated from mRNA.

The term "biologically active adduct" refers to a chemical, molecule or reagent that can perform a function in a cell or an organism. For example the function may include cell proliferation, apoptosis, post-translational modification (e.g., phosphorylation), cell signaling activation, cell signaling inactivation, cell death, cell labeling, etc.

The term "selective incorporating" in the context of protein translation refers to including or introducing a specific amino acid (e.g., a specific non-natural amino acid) in a predetermined, desired amino acid position in the sequence of the protein without disturbing the desired function of the protein.

The phrase "concentration sufficient to permit selective incorporation" refers to a minimal concentration of a component (e.g., RS, non-natural amino acid, amber suppressor tRNA) needed for site-specific incorporation of the non-natural amino acid to a protein of interest.

The term "preferentially aminoacylates" refers to the preference of a tRNA synthase to aminoacylate (charge) a particular tRNA molecule with a predetermined amino acid molecule compared to another amino acid molecule. In other words, the tRNA synthtase can selectively aminoacylate a non-natural amino acid (nnAA) over a naturally occurring amino acid. For example, the tRNA synthtase can aminoacylate a specific nnAA at a frequency of greater than 90%, e.g., 91%, 92%, 93%, 94%, 95%, 96%, 97%, 98%, 99%, or 100%, compared to any or all other natural amino acids.

The term "naturally occurring amino acid" refers to any one of the 20 amino acids encoded by the genetic code, such as, (arginine, Arg, R; histidine, His, H; lysine, Lys, K; aspartic acid, Asp, D; glutamic acid, Glu, E; serine, S, Ser; threonine, Thr, T; asparagine, Asn, N; glutamine, Gln, Q; cysteine, Cys, G; glycine, Gly, G; proline, Pro, P; alanine, Ala, A; isoleucine, Ile, I; leucine, Leu, L; methionine, Met, M; phenylalanine; Phe, F; tryptophan, Trp, W; tyrosine, Tyr, Y, and valine, Val, V, that are precursors to proteins.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid or polynucleotide is used interchangeably with gene, cDNA, and mRNA encoded by a gene.

The term "peptide," "protein," and "polypeptide" are used herein interchangeably and refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins and truncated proteins, wherein the amino acid residues are linked by covalent peptide bonds.

The term "mutein" refers to a protein having an amino acid substitution relative to the wild-type or reference amino acid sequence for the protein.

The term "sequence identity" or "percent identity" in the context of two or more nucleic acids or polypeptide sequences, refers to two or more sequences that are the same or have a specified percentage of amino acid residues or nucleotides that are the same, when compared and aligned for maximum correspondence over a comparison window, as measured using a sequence comparison algorithm, e.g., BLASTP. For purposes of this document, the percent identity is determined over the full-length wild-type sequence such as the reference sequence set forth in SEQ ID NO:1. The method for calculating the sequence identity as provided herein is the BLASTP program having its defaults set at a wordlength (W) of 3, an expectation (E) of 10, and the BLOSUM62 scoring matrix (see, e.g., Henikoff and Henikoff, 1989, *Proc Natl Acad Sci* USA 89:10915). Exemplary determination of sequence alignment and % sequence identity can employ the BESTFIT or GAP programs in the GCG Wisconsin Software package (Accelrys, Madison Wis.), using default parameters provided.

The term "substitution at amino acid position" refers to a change of an amino acid residue at a specific position of the amino acid sequence of a protein. For example, the term "X20Y" refers to the replacement of the wild-type (reference) amino acid X at amino acid position 20 of the protein with the amino acid Y.

The term "suppression codon" refers to a nucleotide triplet that is introduced into a polynucleotide at a predetermined location and is recognized by a specific tRNA that can recognize a stop codon (e.g., an amber, ochre or opal stop codon) and allows translation to read through the codon to produce the protein, thereby suppressing the stop codon.

The term "biologically active protein" refers to a protein that retains at least some of the biological activity of the protein of interest. The biological activity can be determined by comparing the activity, function and/or structure of the protein of interest expressed by the methods described herein to the activity of a reference protein of interest. For example, if the reference protein of interest is an IgG, a biologically active protein will comprise a properly folded and assembled IgG molecule. In some embodiments, the reference protein can be a protein expressed by a bacterial cell free synthesis system that does not contain an exogenous protein chaperone. The biological activity can be determined using an in vitro or in vivo assay that is appropriate for the protein of interest. The biological activity of the protein of interest can be expressed as the biological activity per unit volume of the cell-free protein synthesis reaction mixture. In some embodiments, the biological activity of a protein produced by the methods described herein is at least 30%, 35%, 40%, 45%, 50%, 55%, 60%, 65%, 70%, 70%, 80%, 85%, 90%, 91%, 92%, 93%, 94%, 95%, 96%, 97%, 98%, 99% or 100% of the activity of a reference protein.

The term "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), and single chain Fv antibodies (sFv or scFv) in which a variable heavy and a variable light chain are joined together (directly or through a peptide linker) to form a continuous polypeptide. The single chain Fv antibody is a covalently linked VH—VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The first functional antibody molecules to be expressed on the surface of filamentous phage were single-chain Fv's (scFv); however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see, e.g., U.S. Pat. Nos. 5,091,513, 5,132,405, and 4,956,778). Antibodies also include all those that have been displayed on phage (e.g., scFv, Fv, Fab and disulfide linked Fv (Reiter et al. (1995) Protein Eng. 8: 1323-1331). Antibodies can also include diantibodies, miniantibodies and scFv-Fc fusions.

As used herein, the term "Fab fragment" is an antibody fragment that contains the portion of the full-length antibody that results from digestion of a full-length immunoglobulin with papain, or a fragment having the same structure that is produced synthetically, e.g. recombinantly. A Fab fragment contains a light chain (containing a variable ($V_L$) and constant (CO region domain) and another chain containing a variable domain of a heavy chain ($V_H$) and one constant region domain portion of the heavy chain ($C_{HS}$).

As used herein, a F(ab')$_2$ fragment is an antibody fragment that results from digestion of an immunoglobulin with pepsin at pH 4.0-4.5, or a synthetically, e.g. recombinantly, produced antibody having the same structure. The F(ab')$_2$ fragment contains two Fab fragments but where each heavy chain portion contains an additional few amino acids, including cysteine residues that form disulfide linkages joining the two fragments.

The term "bacterial derived cell free extract" refers to preparation of in vitro reaction mixtures able to transcribe DNA into mRNA and/or translate mRNA into polypeptides. The mixtures include ribosomes, ATP, amino acids, and tRNAs. They may be derived directly from lysed bacteria, from purified components or combinations of both.

The term "cell-free synthesis system" or "CFPS system" refers to the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with unnatural amino acids, polymerases, transcriptional factors, tRNA synthetases, etc.

The term "active oxidative phosphorylation system" refers to a bacterial lysate that exhibits active oxidative phosphorylation during protein synthesis. For example, the bacterial lysate can generate ATP using ATP synthase enzymes and reduction of oxygen. It will be understood that other translation systems known in the art can also use an active oxidative phosphorylation during protein synthesis. The activation of oxidative phosphorylation can be demonstrated by inhibition of the pathway using specific inhibitors, such as electron transport chain inhibitors.

II. DETAILED DESCRIPTION OF EMBODIMENTS

Provided herein are compositions of and methods of producing a RS variant containing amino acid substitutions to wild-type *M. jannaschii* tyrosyl tRNA synthetase as set forth in SEQ ID NO: 1. The RS variants have high activity and increased specificity for the non-natural amino acid pAMF compared to the common naturally occurring amino acids. Provided also are methods of introducing a suppressor codon into a polynucleotide encoding a protein of interest, such that pAMF is incorporated into a specific location in the protein of interest. In addition, methods for producing said protein of interest in a cell-free protein synthesis system are described. Furthermore, methods for conjugating a biologically active adduct to the protein of interest via the non-natural amino acid are described. Exemplary embodiments of producing: 1) a RS variant, 2) a target protein with pAMF at a desired location, and 3) a target protein containing a site-specific pAMF conjugated to a biologically active adduct are found in the Examples.

A. General Methods

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference, for definitions and terms of the art. Standard methods also appear in Bindereif, Schon, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

Methods for protein purification, chromatography, electrophoresis, centrifugation, and crystallization are described in Coligan et al. (2000) Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. Methods for incorporation of non-natural amino acids into proteins using cell-free synthesis are described in Shimizu et at (2006) FEBS Journal, 273, 4133-4140.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., Short Protocols in Molecular Biology, 5$^{th}$ Edition, Wiley, 2002, and Innis et al., PCR Protocols, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., Proc. Natl. Acad. Sci. U.S.A. 87:1663-1667, 1990; Eberwine et al., Proc. Natl. Acad. Sci. U.S.A. 89:3010-3014, 1992).

B. Introducing Amino Acid Substitutions to Wild-Type Aminoacyl-tRNA Synthetase.

Surprisingly, it has been determined that specific amino acid substitutions to wild-type *M. jannaschii* tyrosyl tRNA synthetase allow it to preferentially or selectively incorporate para-methylazido-L-phenylalanine (pAMF) but not any of the common naturally occurring amino acids into nascent proteins during cell-based or cell free protein synthesis. In addition, the synthetase does not aminoacylate any endogenous *E. coli* tRNAs with tyrosine, but can aminoacylate a mutant amber suppressor tRNA. The amino acid substitutions, such as L65A, L65V, F108Y, F108W, D158A, Y32T, Y32V, Y32A, I159S, I159G, I159V, Q109L, Q109M, and Q109I can be made by mutating the coding sequence of the wild-type *M. jannaschii* tyrosyl tRNA synthetase as set forth in SEQ ID NO: 1. The RS variant is generated from a wild-type tyrosyl tRNA synthetase DNA sequence or the portion thereof containing the open reading frame, with changes made as required at the codons corresponding to substitutions described herein.

The amino acid sequence of a specific RS variant provides a description of all polynucleotides capable of encoding the RS variant because of the known correspondence between amino acids and the genetic code. For most organisms the genetic code is "Amino Acid (one letter code) [codons]": phenylalanine (F) [TTT, TTC]; leucine (L) [TTA, TTG, CTT, CTC, CTA, CTG]; isoleucine (I) [ATT, ATC, ATA]; methionine (M) [ATG]; valine (V) [TGG, GTC, GTA, GTG]; serine (S) [TCT, TCC, TCA, TCG, AGT, AGC]; proline (P) [CCT, CCC, CCA, CCG]; threonine (T) [ACT, ACC, ACA, ACG]; alanine (A) [GCT, GCC, GCA, GCG]; tyrosine (Y) [TAT, TAC]; histidine (H) [CAT, CAC]; glutamine (Q) [CAA, CAG]; asparagine (N) [AAT, AAC]; lysine (K) AAA, AAG]; aspartic acid (D) [GAT, GAC]; glutamic acid (E) [GAA, GAG]; cysteine (C) [TGT, TGC]; tryptophan (W) [TGG]; arginine (R) [CGT, CGC, CGA, CGG, AGA, AGG]; and glycine (G) [GGT, GGC, GGA, GGG].

In some instances, the amino acid sequence can differ in one or more amino acids from those of the RS proteins provided herein as a result of one or more of the well-known conservative amino acids substitutions. Conservative substitutions for an amino acid within the RS protein sequence provided herein can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

For example, RS variants provided herein can contain conservative amino acid substitutions, such as, but not limited to, a RS variant with the following amino acid substitutions:

i) M6L, Y32A, L65V, F108W and I159G;
ii) M6L, Y32V, L65V, F108Y and I159V;
iii) M6L, Y32T, L65V, F108W and I159S;
iv) N10Q, Y32A, L65V, F108W and I159G;
v) N10Q, Y32V, L65V, F108Y and I159V;
vi) N10Q, Y32T, L65V, F108W and I159S;
vii) I14L, Y32A, L65V, F108W and I159G;
viii) I14L, Y32V, L65V, F108Y and I159V;
ix) I14L, Y32T, L65V, F108W and I159S;
x) S16T, Y32A, L65V, F108W and I159G;
xi) S16T, Y32V, L65V, F108Y and I159V;
xii) S16T, Y32T, L65V, F108W and I159S, and the like.

The RS variants of this invention are further defined by their ability to bind to polyclonal antibodies generated against the wild-type TyrRS having the amino acid sequence of SEQ ID NO: 1. Under designated immunoassay conditions, the RS variants of this invention include those defined by their function, i.e., their ability selectively incorporate the non-natural amino acid and by their ability to also bind to the specified polyclonal antibodies at a rate of at least two times above the background. Typically a specific or selective reaction will be at least twice background signal or noise and more typically more than 10 to 100 times background. A variety of immunoassay formats may be used to determine if the test polyclonal antibodies react with an aaRS of this invention. See, e.g., Harlow & Lane, Antibodies, A Laboratory Manual (1988) for a description of immunoassay formats and conditions that can be used to determine specific immunoreactivity.

Methods for generate a coding sequence encoding a RS variant with amino acid substitutions include standard molecular cloning techniques such as, but not limited to, PCR, mutagenesis, and restriction enzyme cloning. Alternatively, the coding sequence of RS variants can be produced using synthetic chemistry according to standard methods, e.g., the solid phase phosphoramidite triester method.

It is recognized by those skilled in the art that various well-known mutagenesis techniques are available to generate the RS variants of this invention. For instance, point mutations corresponding to the desired amino acid substitutions described herein can be introduced to the coding sequence for wild-type *M. jannaschii* tyrosyl tRNA synthetase by overlapping PCR. Alternatively, the wild-type coding sequence can be mutated using a PCR-based mutagenesis technique, e.g., site-directed mutagenesis, to mutate the codons corresponding to the desired amino acid substitutions of the RS variants. The desired polynucleotide encoding the RS variant is used to generate the RS variant protein.

More specifically such mutagenesis techniques include, e.g., site-directed mutagenesis (e.g., QuikchangeII™ Site Directed Mutagenesis kit, Agilent Technologies), random mutagenesis (Diversify™ PCR Random Mutagenesis Kit, Clontech), homologous recombinations, oligonucleotide-directed mutagenesis (e.g., Transformer™ Kit, Clontech), phosphorothioate-modified DNA mutagenesis, etc., can be used to generate a coding sequence corresponding to amino acid substitutions. See, e.g., Ling, et al., "Approaches to DNA mutagenesis: an overview," *Anal. Biochem.*, 254(2):

157-78 (1997); Dale, et al., "Oligonucleotide-directed random mutagenesis using the phosphorothioate method," *Methods Mol. Biol.*, 57:369-74 (1996); Smith, "In vitro mutagenesis," *Ann. Rev. Genet.*, 19:423-462 (1985); Botstein, et al., "Strategies and applications of in vitro mutagenesis," *Science*, 229:1193-1201 (1985); Carter, "Site-directed mutagenesis," *Biochem. J.*, 237:1-7 (1986); Kramer, et al., "Point Mismatch Repair," *Cell*, 38:879-887 (1984); Wells, et al., "Cassette mutagenesis: an efficient method for generation of multiple mutations at defined sites," *Gene*, 34:315-323 (1985); Minshull, et al., "Protein evolution by molecular breeding," *Current Opinion in Chemical Biology*, 3:284-290 (1999); Christians, et al., "Directed evolution of thymidine kinase for AZT phosphorylation using DNA family shuffling," *Nature Biotechnology*, 17:259-264 (1999); Crameri, et al., "DNA shuffling of a family of genes from diverse species accelerates directed evolution," *Nature*, 391:288-291; Crameri, et al., "Molecular evolution of an arsenate detoxification pathway by DNA shuffling," *Nature Biotechnology*, 15:436-438 (1997); Zhang, et al., "Directed evolution of an effective fucosidase from a galactosidase by DNA shuffling and screening," *Proceedings of the National Academy of Sciences, U.S.A.*, 94:45-4-4509; Crameri, et al., "Improved green fluorescent protein by molecular evolution using DNA shuffling," *Nature Biotechnology*, 14:315-319 (1996); Stemmer, "Rapid evolution of a protein in vitro by DNA shuffling," *Nature*, 370:389-391 (1994); Stemmer, "DNA shuffling by random fragmentation and reassembly: In vitro recombination," *Proceedings of the National Academy of Sciences, U.S.A.*, 91:10747-10751 (1994); WO 95/22625; WO 97/0078; WO 97/35966; WO 98/27230; WO 00/42651; WO 01/75767; and WO 2009/152336, all of which are incorporated herein by reference.

C. Expressing Aminoacyl-tRNA Synthetases Specific for Para-Methylazido-L-Phenylalanine.

Once the desired RS variant polynucleotide is obtained, it can be used to generate the corresponding polypeptide in a cell-based or a cell free expression system.

In a cell-based protein synthesis system, the polynucleotide encoding the RS variant is cloned into an expression vector such as a plasmid, phage, phagemid, cosmid, bacteriophage, baculovirus vector, yeast plasmid, and the like. The expression vector can include the nucleic acid of the present invention that is operably linked to a promoter. Subsequently, the expression vector is introduced into a host cell to express the RS variant. Any other vector may be used as long as it is replicable and viable in the host cell. The host cell can be a bacterial cell, an archaeal cell, a fungal cell, a yeast cell, an insect cell, or a mammalian cell. The RS variant can be produced in a cell and then purified from the cell lysate.

In a cell-free protein synthesis (CFPS) system, the polynucleotide encoding the RS variant serves as the polynucleotide template for the reaction. Other components of the reaction include one or more bacterial extracts and/or defined reagents. The reaction mix can also include at least ATP or an energy source, co-factors, enzymes and other reagents that are necessary for polypeptide synthesis, e.g., ribosomes, tRNA, polymerases, transcriptional factors, aminoacyl synthetases, elongation factors, initiation factors, etc. Further description of exemplary CFPS reaction systems are described below.

The RS variant protein can be purified following protein synthesis according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. C. Janson and Lars Ryden, editors, VCH Publishers, New York, 1989) to obtain substantially pure polypeptides.

The activity and selectivity of the RS variant to charge the suppressor tRNA with the non-native amino acid can be determined by using a reporter gene containing a suppressor codon. The activity of the RS variant in the presence of pAMF compared to the 20 common naturally occurring amino acids can be measured by detecting the presence or absence of the reporter protein. A description of methods for introducing a suppressor codon into a polynucleotide encoding a target protein such as a reporter protein is provided below.

A positive selection reporter (e.g., a fluorescent reporter, luminescent reporter, or affinity-based reporter) can be used such that amber suppression results in a detectable, positive signal. For example, an amber codon can be introduced into the reporter gene (e.g., GFP gene). If the RS variant is able to charge the suppressor tRNA in the presence of pAMF, GFP is detected, thereby indicating that the RS variant is specific for the amber codon and pAMF. If the RS variant is unable to charge the suppressor tRNA in the presence of pAMF, functional GFP protein is not translated due to the premature stop codon inserted into the GFP reporter gene. Moreover, if the RS variant can charge the suppressor tRNA in the absence of pAMF, the variant is not specific for the nnAA. See, e.g., Example 1 and Takimoto et al., *Molecular Biosystems*, 5:931-934 (2009). In other instances, the selection marker can be a resistance gene containing an amber stop codon in the gene, such that in the presence of a selection agent (e.g., antibiotic, antibody, nutrient, and the like), cells contain a RS variant effective at codon suppression can be distinguished from those without an functional RS variant.

D. Introducing Suppressor Codons into Polynucleotides Encoding Proteins of Interest.

Once the desired aaRS protein is obtained, it is necessary to generate a target polynucleotide encoding a target protein with a desired site for pAMF. Provided herein are methods for introducing a suppressor codon (e.g., amber TAG, ochre TAA, opal TGA) that is recognized by the RS variant described herein into the polynucleotide encoding a protein of interest. Non-limiting examples of a protein of interest include an antibody, antibody fragment, anti-idiotype antibody, chimeric antibody, humanized antibody, antibody fusion protein, secreted protein (e.g., hormone), transmembrane protein (e.g., receptor), enzyme, proprotein, protein fragment, pharmaceutically active protein, and a protein having potential industrial or therapeutic value. In some embodiments, the protein of interest is an antibody or an antibody fragment.

The coding region of the polynucleotide can be mutated to introduce a suppressor codon, e.g., an amber codon TAG into the open reading frame of the polynucleotide encoding the protein of interest such that the RS variant described herein can selectively suppress the introduced codon during translation and generate the protein of interest containing a non-natural amino acid at a desired location. The mutation can be introduced to avoid changing the open reading frame of the protein. For example, the polynucleotide encoding the protein of interest is mutated to insert a suppressor codon into the coding region of the protein in a selected position, such that the protein of interest contains the non-natural amino acid and is produced with the aid of the RS variant/suppressor tRNA pair. The position of the suppressor codon can be selected according to the primary, secondary, tertiary or quarternary structure of the protein, the function of the protein, the non-amino acid to be incorporated into the protein, and/or the biologically active adduct to be conjugated to the protein.

Methods for introducing a suppressor codon into the polynucleotide encoding the protein of interest include, but are not limited to, standard molecular biology techniques such as PCR, cloning and mutagenesis. As described above, useful mutagenesis techniques include, but are not limited to, site-directed mutagenesis (e.g., QuikchangeII™ Site Directed Mutagenesis kit, Agilent Technologies), random mutagenesis (Diversify™ PCR Random Mutagenesis Kit, Clontech), homologous recombinations, oligonucleotide-directed mutagenesis (e.g., Transformer™ Kit, Clontech), phosphorothioate-modified DNA mutagenesis, etc., can be used to generate amino acid substitutions, etc., can be used to generate amino acid substitutions. Other mutagenesis techniques are described above.

The mutated polynucleotide containing the suppressor codon can be cloned into an expression vector such as a plasmid, phage, phagemid, cosmid, bacteriophage, baculovirus vector, yeast plasmid, and the like. The expression vector can include the nucleic acid of the present invention that is operably linked to a promoter. Subsequently, the expression vector is introduced into a host cell to express the modified protein of interest. Any other vector may be used as long as it is replicable and viable in the host cell. The host cell can be a bacterial cell, an archaeal cell, a fungal cell, a yeast cell, an insect cell, or a mammalian cell.

The mutated polynucleotide encoding the protein of interest can be used a in a cell-free protein synthesis (CFPS) reaction for producing the protein of interest with a site-specific non-natural amino acid pAMF.

E. Cell Free Protein Synthesis (CFPS) of pAMF-Containing Proteins.

After generating both the desired RS variant and the target polynucleotide encoding a target protein with a desired site for pAMF, it is possible to synthesize the pAMF-containing target protein. Provided herein are methods of cell free protein synthesis for incorporating para-methylazido-L-phenylalanine into the protein of interest. In particular, the CFPS reaction includes para-methylazido-L-phenylalanine in a concentration sufficient to permit selective incorporation of pAMF into the protein of interest, a polynucleotide having a coding region encoding the protein of interest and including a suppression codon selectively positioned within its coding region, a tRNA able to be charged with pAMF and complementary to the suppression codon of the protein of interest, and the RS variant provided herein.

The amount of purified *M. jannaschii* RS variant protein in the CFPS reaction can be in the range of about 1 µM to about 10 µM, e.g., 1 µM, 2 µM, 3 µM, 4 µM, 5 µM, 6 µM, 7 µM, 8 µM, 9 µM or 10 µM.

In some instances, the amount of RS variant protein used is in excess of the amount need to aminoacylate the orthogonal amber suppressor tRNA. The amount of RS variant protein in the CFPS reaction can be in the range of about 1 µM to about 10 µM, e.g., 1 µM, 2 µM, 3 µM, 4 µM, 5 µM, 6 µM, 7 µM, 8 µM, 9 µM or 10 µM.

The amount of para-methylazido-L-phenylalanine in the CFPS reaction can be in the range of about 1 mM to about 10 mM, e.g., 1 mM, 2 mM, 3 mM, 4 mM, 5 mM, 6 mM, 7 mM, 8 mM, 9 mM or 10 mM.

Cell free protein synthetic reaction systems are well-known in the art, and have been described in, e.g., Zawada et al., 2011, *Biotechnol. Bioeng.*, 108(7):1570-1578; Shimizu et al., *Nature Biotechnology*, 2001, 19:751-755; and U.S. Pat. Nos. 7,338,789 and 8,492,115, the disclosures of which are incorporated by reference in their entirety for all purposes.

Cell free protein synthesis (CFPS) systems utilize cell extracts to support the synthesis of proteins in vitro from purified mRNA transcripts or from mRNA transcribed from DNA during the in vitro synthesis reaction. The reaction mixture is capable of catalyzing the synthesis of polypeptides from a nucleic acid template. The mixture includes one or more bacterial extracts and/or defined reagents. Exemplary bacterial extracts include, but are not limited to, *E. coli* S30 extracts, OmpT sensitive RF-1 attenuated *E. coli* extract, and variants thereof. The bacterial cells of the extract can overexpress a component of the CFPS system such as enzymes, e.g., DsbA, PpiA, FkpA, DegP and SlyD, and tRNAs (e.g., an orthogonal suppressor-encoding tRNA such as an orthogonal CUA-encoding tRNA).

Methods of preparing a cell extract for CFPS are described in, e.g., Zawada, J. "Preparation and Testing of *E. coli* S30 In Vitro Transcription Translation Extracts", Douthwaite, J. A. and Jackson, R. H. (eds.), *Ribosome Display and Related Technologies: Methods and Protocols, Methods in Molecular Biology*, vol. 805, pp. 31-41 (Humana Press, 2012); Jewett et al., *Molecular Systems Biology:* 4, 1-10 (2008); Shin J. and Norieaux V., *J. Biol. Eng.*, 4:8 (2010). Briefly, a bacterial culture is grown and harvested; suspended in an appropriate buffer (e.g., S30 buffer), and homogenized to lyse the cells.

The reaction mix of the CFPS system can also include at least ATP or an energy source; a template for production of the macromolecule, e.g., DNA, mRNA, etc.; amino acids, and such co-factors, enzymes and other reagents that are necessary for synthesis of the protein of interest, e.g., ribosomes, tRNAs (including orthogonal suppressor-encoding tRNA), polymerases, transcriptional factors, aminoacyl synthetases (e.g., RS variant provided herein), chaperones, elongation factors, initiation factors, etc.

When the suppressor codon is an amber codon, it is useful for the reaction mixture to include a component that can attenuate release factor (RF) activity or has decreased activity, e.g., a RF-1, RF-2 or RF-3 mutant. It is recognized by one skilled in the art that suppression efficiency of the amber suppressor tRNA is dependent on competition with the release factor 1 (RF1) for decoding the amber codon by the ribosome. RF1 acts to terminate the polypeptide chain at the stop codon, while the amber suppressor tRNA competes with RF1 to incorporate the non-natural amino acid during protein synthesis. Thus, decreasing the amount or activity of RF1 in the CFPS system can increase the suppression efficiency of the charged suppressor tRNAs. RF1 activity can be manipulated by using, e.g., RF1 inhibitory aptamers, antibodies against RF1, and RF-1 depleted cell lysates. In some instances, RF1 is omitted from the CFPS system.

The CFPS system can include an energy source such as a homeostatic energy source. Also included may be enzyme(s) that catalyze the regeneration of ATP from high-energy phosphate bonds, e.g., acetate kinase, creatine kinase, etc., via oxidative phosphorylation. Such enzymes may be present in the extracts used for translation, or may be added to the reaction mix. Optionally, a compound such as nicotinamide adenine dinucleotide (NADH), $NAD^+$ or acetyl-coenzyme A can be added for activation of oxidative phosphorylation.

To synthesize a protein of interest in vitro, a CFPS extract at some point comprises a mRNA molecule that encodes the protein of interest and contains a selectively positioned suppression codon (e.g., an amber codon). In some CFPS systems, mRNA is added exogenously after being purified from natural sources or prepared synthetically in vitro from cloned DNA using RNA polymerases such as RNA polymerase II, SP6 RNA polymerase, T3 RNA polymerase, T7 RNA polymerase, RNA polymerase III and/or phage derived RNA polymerases. In other systems, the mRNA is produced in vitro from a template DNA polynucleotide; both transcription and translation occur in this type of CFPS reaction. The template DNA contains a suppression codon selectively positioned with in the coding region. In yet other systems, transcription and translation systems are coupled or complementary transcription and translation systems, which carry out the synthesis of both RNA and the protein of interest in the same reaction, have been developed. In such in vitro transcription and translation systems, the CFPS extracts contain all the components (exogenous or endogenous) necessary both for transcription (to produce mRNA) and for translation (to synthesize the protein of interest) in a single system.

In some embodiments, the CFPS reaction is performed using the Cytomim™ system comprising NTPs, *E. coli* tRNAs and an orthogonal suppressor-encoding tRNA, amino acids and pAMF, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, sodium pyruvate, NAD, CoA, $Na^+$ oxalate, putrescine, spermidine, and bacterial extract. In some embodiments, the energy substrate for the Cytomim™ system is pyruvate, glutamic acid, and/or glucose. In some embodiments of the system, the nucleoside triphosphates (NTPs) are replaced with nucleoside monophosphates (NMPs).

In some embodiments, the CFPS reaction is performed using the PANOx-SP system comprising NTPs, tRNAs and an orthogonal suppressor-encoding tRNA, amino acids and pAMF, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, phosphoenol pyruvate (PEP), NAD, CoA, $Na^+$ oxalate, putrescine, spermidine, and S30 extract.

To incorporate a para-methylazido-L-phenylalanine into a protein of interest, the CFPS system includes the *M. jannaschii* RS variant protein of the present invention, a tRNA able to be charged with pAMF and complementary to the suppression codon of the protein of interest, a polynucleotide having a coding region encoding the protein of interest and harboring a suppressor codon (e.g., amber codon) selectively positioned within the coding region, and para-methylazido-L-phenylalanine. The non-natural amino acid can be synthetic or derived from another biological source. For instance, para-methylazido-L-phenylalanine can be synthesized according to the method described in Example 2.

The protein of interest bearing the non-natural amino acid can be purified according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., PROTEIN PURIFICATION, J. C. Janson and Lars Ryden, eds., VCH Publishers, New York, 1989) to obtain substantially pure polypeptides.

The incorporation of the para-methylazido-L-phenylalanine residue can be determined by methods such as, mass spectometry, protein sequencing, amino acid tagging such as by fluorescence, radioactivity, ELISA or other antibody screening assays, functional assays, or other methods known to one skilled in the art.

In some embodiments, the method further includes the step of conjugating a biologically active adduct to the pAMF of the protein of interest. In some instances, the conjugation is by a 1,3-cycloaddition of an azide with a strained alkyne.

F. Conjugation Chemistry for pAMF-Containing Proteins.

Having the target protein containing pAMF at the desired amino acid location, a biologically active adduct can be conjugated to the pAMF using a chemical reaction such as click chemistry. For instance, the pAMF containing protein of interest is purified by standard procedures, and then the purified protein is subject to a click chemistry reaction (e.g., copper(I)-catalyzed azide-alkyne 1,3-cycloaddition reaction or copper-free catalyzed azide-alkyne 1,3-cycloaddition reaction) to directly conjugate a biologically active adduct to the pAMF residue.

Exemplary biologically active adducts for use in the present invention include, not are not limited to, small molecules, oligonucleotides, peptides, amino acids, nucleic acids, sugars, oligosaccharides, polymers, synthetic polymers, chelators, fluorophores, chromophores, other detectable agents, drug moieties, cytotoxic agents, detectable agents, and the like.

Detailed descriptions of a click chemistry reaction for conjugation of a biologically active adduct are found in, e.g., Baskin et al., *Proc. Natl. Acad. Sci.*, 2007, 104: 16793-16797; Kim et al., *Curr. Opin. Chem. Biol.*, 2013, 14:412-419; and Bundy and Swartz, *Bioconjug. Chem.*, 2010, 21(2): 255-263.

In a click chemistry reaction, alkynes are activated for [3+2] cycloaddition with azides. The biologically active adduct containing (e.g., linked to) a strained alkyne (e.g., cyclooctyne or variant thereof) can undergo strain-promoted alkyne-azide cycloaddition with the non-natural amino acid para-methylazido-L-phenylalanine on the protein of interest, thereby conjugating the biologically active adduct to the protein at the amino acid position of the non-natural amino acid. A preferred strained alkyne reagent is the reagent DBCO, shown below.

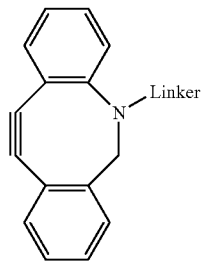

The conjugated protein of interest can be purified according to standard methods known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

The conjugated protein of interest can be quantitated according to standard methods known in the art including, but not limited to, mass spectrometry (e.g., ESI-TOF mass spectrometry and tanden mass spectometry), microfluidic electrophoresis, gel electrophoresis, Western blotting, immunoassays (e.g., ELISA), and other assays to assess the activity of the conjugated protein.

III. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Generating
Para-Methylazido-L-Phenylalanine (pAMF)-Specific
TyrRS Variants and Determining Suppression
Efficiency This example illustrates a method of screening for novel pAMF-specific RS variants for use in a cell-free protein synthesis system. A detailed description of the method is found in, for example, Zimmerman et al., *Bioconjugate Chemistry*, 2014, 25, 351-361, which is hereby incorporated by reference in its entirety for all purposes.

The pAMF-specific RS variants described herein such as those containing the following amino acid substitutions: A1) Y32T, L65A, F108Y, Q109L and I159S; A4) Y32V, L65A, F108W, Q109M and I159G; B03) Y32A, L65V, F108W and I159G; C10) Y32V, L65V, F108Y and I159V; D08) Y32T, L65V, F108W and I159S; and C02) Y32V, L65V, F108W, G109I and I159S were generated by PCR and expressed in *E. coli* cells. Briefly, overlap extension PCR with primers specific for each designed mutation was used to construct the aaRS variants. The PCR products were ligated into a T7-promoter driven expression vector (e.g., pYD317) and used to transform *E. coli* cells. The final aaRS coding sequence contained an in-frame, carboxy terminal hexahistidine tag to facilitate downstream protein purification and biochemical characterization. Purified plasmid DNA from the colonies was used as DNA templates for T7 DNA polymerase-driven aaRS expression in small scale (e.g., 100 µl) cell-free protein synthesis (CFPS) reactions (see, e.g., Zawada et al., 2011, *Biotechnol. Bioeng.*, 108(7), 1570-1578). The CFPS reactions were performed using a cell extract that contained an amber suppressor tRNA that is recognized by *M. jannaschii* TyrRS and had been optimized for high expression and low toxicity in the extract strain used. These reactions were used as a source of aaRS for the amber suppression reporter reactions, as described below, to assess the activity and selectivity of the pAMF-specific RS variant proteins.

The amber suppression reporter assays are based on cell free protein synthesis reactions using the amber suppressor reporter GFP gene. In particular, the amber suppression reporter reactions expressed GFP with an amber TAG codon at lysine 49 (K49TAG) of the reporter gene TurboGFP (Evrogen, Moscow, Russia). Lysine 49 is in a solvent-exposed loop, and is a permissive site which allows for GFP fluorescence regardless of the amino acid present at this position. Comparison of GFP fluorescence in the presence of pAMF versus the absence of pAMF was used to indicate the specificity of the aaRS toward the nnAA and its ability to discriminate against any of the 20 common natural amino acids.

The amber suppression reporter reactions were performed as follows: 4 µl of the synthetase production CFPS as described above was added to a 20 µl GFP K49TAG reporter CFPS reaction in 384-well black microtiter places in the absence of pAMF or in the presence of 1 mM pAMF. After 12 hours of expression at 30° C. for 12 hours the end point GFP fluorescence signal was measured at excitation at 476 nm, emission at 510 nm on a SpectraMax M5 fluorescence plate reader. The synthetase variants showed the desired high activity and selectivity toward pAMF, exhibiting at least 3-fold higher suppression efficiency in the presence of pAMF than in the absence of pAMF. The variants showed a high degree of GFP amber suppression only in the presence of pAMF. The variants tested had high selectivity for the non-natural amino acid pAMF, while discriminating against the 20 common natural amino acids. The RS variants A01, B04, B03, C02, C10 and D08 had high suppression efficiencies in the presence of pAMF and substantially no suppression of GFP fluorescence in the reactions lacking pAMF (FIG. 1).

In summary, this example shows that several RS mutant proteins (e.g., muteins) can be used for site-specific incorporation of pAMG with high translational fidelity into proteins in response to the amber codon, TAG.

Example 2. Generating Antibody-Drug Conjugates
(Trastuzumab-MMAF Conjugates) Using Cell-Free
Protein Synthesis of
Para-Methylazido-L-Phenylalanine Containing
Antibodies This example illustrates the use of the aminoacyl-tRNA synthetase (RS) described herein for the production of antibody drug-conjugates through site-specific incorporation of para-methylazido-L-phenylalanine into the antibody trastuzumab. The example also describes the conjugation of a DBCO-PEG-monomethyl auristatin (DBCO-MMAF) drug to the tumor-specific IgG trastuzumab through the non-natural amino acid and copper-free click chemistry. The resulting site-specific antibody drug-conjugate (ADC) displayed a high drug-to-antibody ratio (DAR) and a homogeneous conjugation profile. Importantly, the ADCs were highly potent and specific in in vitro cell cytotoxicity assays.

A. Synthesis of Para-Methylazido-L-Phenylalanine.

It has been shown that the non-natural aminoacid para-azido-L-phenylalanine (pAzF) can be incorporated into proteins such as dihydrofolate reductase (DHFR) and that the pAzF-containing DHFR can be conjugated to a fluorescent dye in a copper(I)-catalyzed (3+2) cycloaddition reaction. Described herein is a novel non-natural amino acid and the use thereof for improved 1) overall product yield, 2) non-natural amino acid incorporation efficiency, and 3) conjugation efficiency of bio-orthogonally conjugated non-natural amino acid-containing proteins.

To generate para-azidomethyl-L-phenylalanine (pAMF), pAzF was modified by the insertion of a methylene spacer between the azido group and the phenyl ring to increase the reactivity of the azido group by breaking the resonance within the phenyl ring system. It was reasoned that addition of a methylene group between the phenyl ring and the para-position azide group would move the azide group away from the potentially electron-withdrawing phenyl ring, thus favoring the copper-free click reaction. In addition, once incorporated into a protein of interest, the methylene spacer could position the azide group further away from the protein surface, thereby decreasing the potential for local electrostatic or steric hindrances to chemical conjugation.

The following scheme shows the synthesis reaction for para-azidomethyl-L-phenylalanine (pAMF).

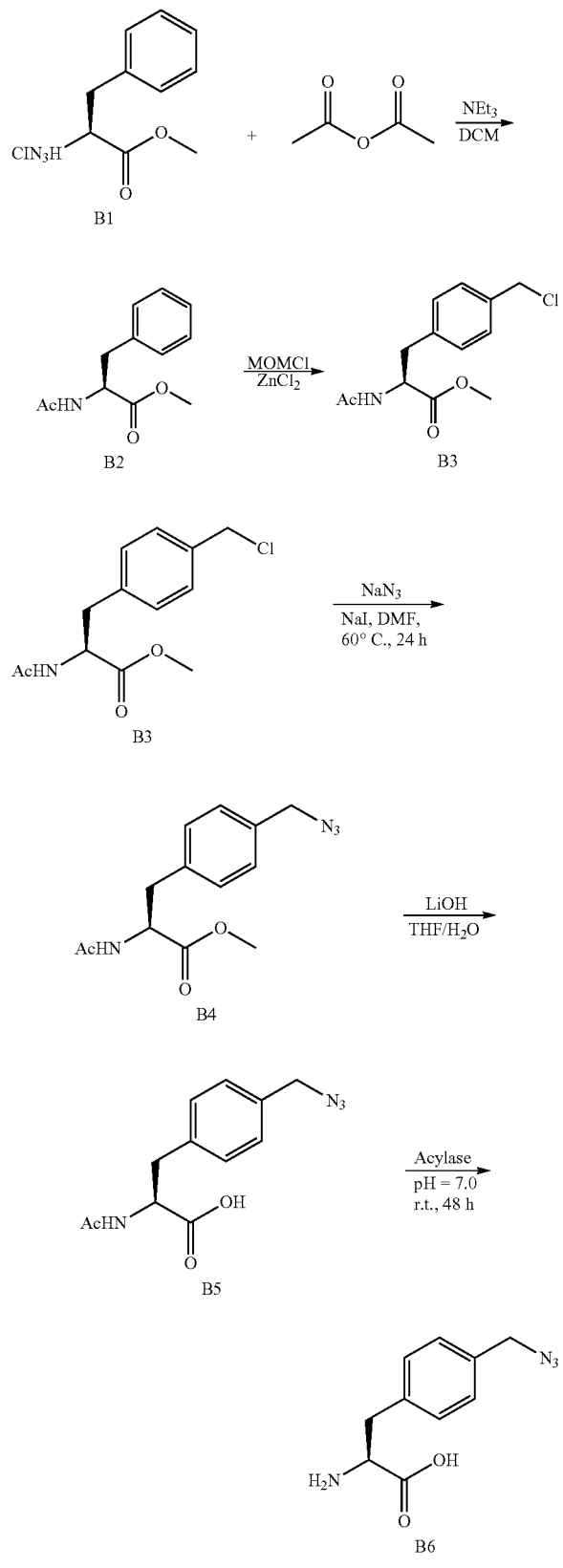

To a solution of the Phe methyl ester B1 (50 g, 232 mmol, 1.0 eq) in DCM (300 mL) was added triethylamine (81 mL, 580 mmol, 2.5 eq) at 0° C. was added acetic anhydride (33 mL, 348 mmol, 1.5 eq) dropwise over 15 min. The mixture was stirred at 25° C. for 3 h. The reaction was washed with NaHCO$_3$ (2×), dried over Na$_2$SO$_4$ and purified by a silica gel column (DCM:MeOH=9:1) to give product B2 (50 g, 97%) as white solid. A mixture of ester B2 (52 g, 0.235 mole, 1.0 eq), MOM-Cl (136 mL, 1.79 mole, 7.6 eq) and ZnCl$_2$ (128 g, 0.94 mole, 4.0 eq) was stirred at 6-8° C. for 8 h. After removing the volatiles on a rotavapor at 6-8° C., the residue was poured into ice-water and extracted with ethyl acetate (3×). The combined organic layers were washed with NaHCO$_3$ and dried over Na$_2$SO$_4$, and concentrated to a small volume. Ether (50 mL) was then added. The ether solution was kept in a −20° C. fridge overnight. The crystallized product was filtered and dried in vacuum to give product B3 (31 g, 49%) as white solid.

To a solution of B3 (20 g, 74.2 mmol, 1.0 eq) in DMF (100 mL) was added NaN$_3$ (9.64 g, 148 mmol, 2.0 eq) and NaI (1.11 g, 7.42 mmol, 0.1 eq). The reaction mixture was heated at 60° C. in an oil-bath overnight. Solvent DMF was removed on a rotavapor, and the reaction mixture was dissolved in ethyl acetate, and washed with NaHCO$_3$ (3×), dried over Na$_2$SO$_4$, and purified by silica gel column (DCM:MeOH=9:1) to give product B4 (20.5 g, 100%) as yellow oil.

To a solution of B4 (20 g, 724 mmol, 1.0 eq) in a mixed solution of THF:MeOH:H$_2$O (50 mL:50 mL:20 mL) was added LiOH—H$_2$O (6.94 g, 144.8 mmol, 2 eq). The reaction was stirred at 25° C. for 2 h. Solvent was removed to give a residue, which was worked up with ethyl acetate. The organic layer was washed with 1N HCl (3×), dried over Na$_2$SO$_4$ and concentrated to give product B5 (18.3 g, 96%) as yellow oil.

To a solution of above amide B5 (18 g, 68.7 mmol) in DMSO (20 mL) and 50 mM NaH$_2$PO$_4$—Na$_2$HPO$_4$ buffer (1.8 L) was added acylase (1 g). The solution was heated at 37° C. for 48 h. Charcoal (20 g) was added into the reaction mixture, and stirred at 25° C. for 10 min and then filtered through Celite. The filtrate was washed with ethyl acetate. The aqueous layer was concentrated to a small volume, and product was precipitated out as white solid. The solid was filtered and dried in vacuo to give product B6 (10 g, 66%) as white solid.

Analysis of product: LC-MS (ESI): 221 (M+1). $^1$HNMR (300 MHz, DMSO-d6) δ 7.27 (br s, 4H), 4.37 (s, 2H), 3.43 (m, 2H), 3.17 (m, 1H), 2.84 (m, 1H).

The small molecule conjugation kinetics of pAzF and pAMF were compared. In particular, pAzF and pAMF were reacted at increasing concentrations with a 10-fold molar excess of dibenzocyclooctyl-polyethylene glycol (DBCO-PEG) compound (FIG. 2A and FIG. 2C) in a copper-free click reaction. First-order kinetics at 25° C., ionic strength 0.5 M (KCl), and 0.005% Tween-20 in phosphate buffer were determined under pseudo-first-order conditions in triplicate, using a SpectraMax M5 plate reader with 96-well polystyrene plates (Molecular Devices, Sunnyvale, Calif.). The formation of conjugated product was measured by the decrease in absorbance of the strained cyclooctoalkyne DBCO at 306 nm in the presence of increasing concentrations of pAzF or pAMF. The second-order rate constants were calculated according to kcat (M−1 sec−1)=kobs/

[Azido]. The reaction rate for pAMF was seven-fold higher than that for pAzF (FIG. 2B). The data shows that pAMF is more reactive than pAzF in copper-free click conjugation reactions.

B. Cell-Free Protein Synthesis System for Producing Para-Methylazido-L-Phenylalanine Containing Antibodies.

The RS variants described in Example 1 were used to incorporate the non-natural amino acid pAMF into the Her2-specific monoclonal antibody trastuzumab. The antibody was expressed in a cell-free protein synthesis reaction as described in Zawada et al., 2011, *Biotechnol. Bioeng.*, 108(7), 1570-1578 with the following modifications. The cell-free extracts were prepared from an OmpT sensitive RF-1 attenuated strain that was also engineered to overexpress *E. coli* DsbC, and a similar RF-1 attenuated *E. coli* strain that was engineered to produce an orthogonal CUA-encoding tRNA for insertion of a non-natural amino acid at an amber stop codon. The cell-free extracts were blended (at a ratio of 85:15), treated with 50 μM iodoacetamide for 30 min at RT (20° C.), and then added to a premix containing all other components of a cell-free protein synthesis system except for DNA encoding IgG heavy and light chains. The final concentration in the cell-free protein synthesis reaction was 30% cell extract, 2 mM para-methylazido-L-phenylalanine (pAMF) (RSP Amino Acids, Shirley, Mass.), 5 μM pAMF-specific RS variant of Example 1 (e.g., A01, B04, B03, C02, C10 or D08 variant), 2 mM GSSG, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNAP, 2 μg/mL trastuzumab light chain DNA, 8 μg/mL trastuzumab-(His)6 heavy chain DNA containing an amber codon at the S136 site (S136TAG). The cell-free synthesis reactions were initiated by the addition of the plasmid DNA encoding the IgG heavy and light chain. The reactions were incubated at 30° C. for 12 h on a shaker at 650 rpm in 48-well Flower plates (m2p-labs # MTP-48-B). The reaction was incubated further at 4° C. for 6 h until it was processed for purification.

C. Purifying Para-Methylazido-L-Phenylalanine Containing Antibodies.

Following the cell-free protein synthesis reaction, the mixture containing para-methylazido-L-phenylalanine containing antibodies was transferred to a 96-well plate (DyNa Block™, 2 mL; Labnet, Edison, N.J.) and centrifuged at 5000×g for 15 minutes at 40° C. Purification of IgG from the cell-free supernatant was carried out by using IMAC Phytips (Phynexus, San Jose, Calif.) containing 40 μL resin. The resin bed was pre-equilibrated in IMAC equilibration buffer (50 mM Tris pH 8.0, 300 mM NaCl, and 10 mM imidazole) and the clarified supernatant was pipetted up and down 10 times through equilibrated IMAC Phytips at a flow rate of 4.2 μL/min. The bound protein was washed with IMAC equilibration buffer, and then eluted with 125 μL IMAC elution buffer (50 mM Tris pH 8.0, 300 mM NaCl, and 500 mM imidazole).

Quantification of purified IgG and analysis of aaRS concentration and purity were performed using microfluidic electrophoresis, e.g., a Protein Expression Chip assay on the LabChip GXII system (Caliper LifeSciences/Perkin Elmer). The assay reagents were prepared per the manufacturer guidelines and run using the Low Sensitivity mode. Samples (2 μL) were mixed with 7 μL Protein Express Sample Buffer using a 96-well PCR plate, denatured at 65° C. for 10 mm and mixed with 32 μL Milli-Q water. For quantification, a Herceptin® or *M. jannaschii* TyrRS standard curve ranging from 500 to 10 μg/mL was prepared in an identical manner to the analyzed samples. The 96-well PCR plate was run on the LabChip GXII and samples were quantified using LabChip GX software v3.1 (Caliper LifeSciences/Perkin Elmer).

D. Chemical Conjugation of Para-Methylazido-L-Phenylalanine Containing Antibodies to Form Antibody-Drug Conjugates.

The DBCO-PEG-monomethyl auristatin (DBCO-MMAF) drug was conjugated to pAMF-containing trastuzumab using copper-free click chemistry. The following scheme shows the chemical synthesis reaction for DBCO-PEG-MMAF (referred to below as AB3627).

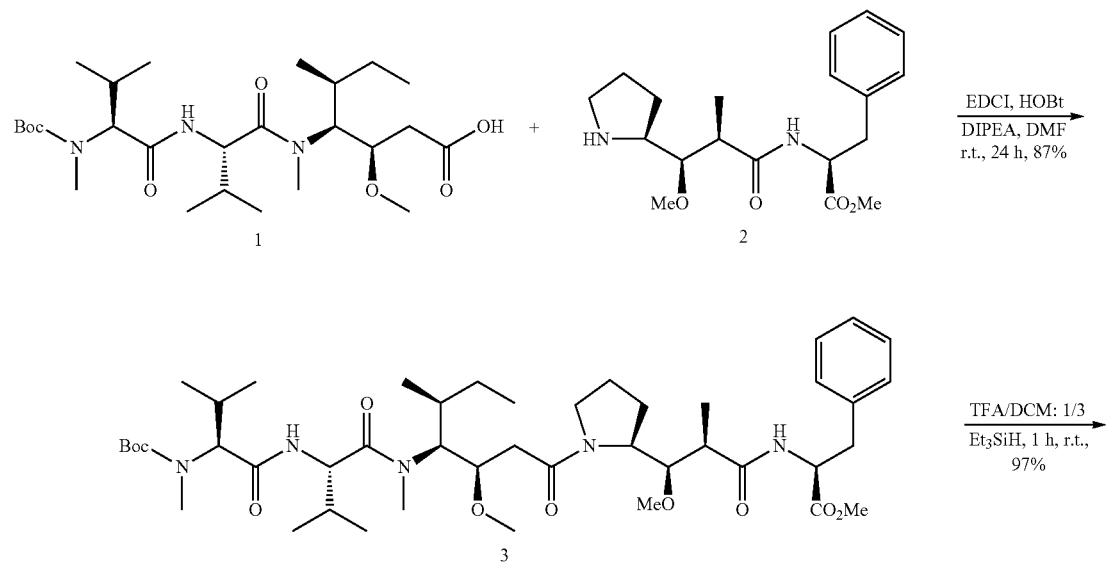

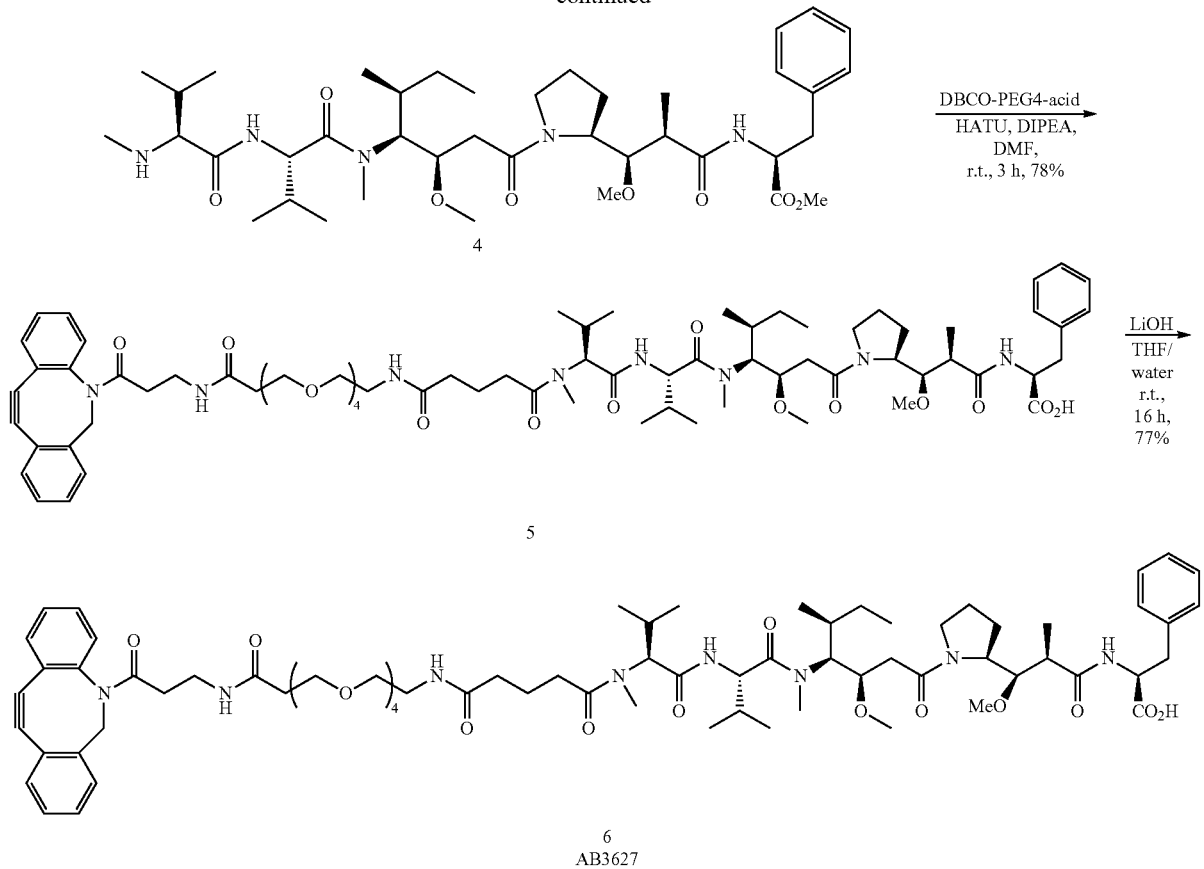

To a solution of an acid 1 (410 mg, 0.80 mmol, 1.0 eq), an airline 2 (279 mg, 0.80 mmol, 1.0 eq) and DIPEA (357 µL, 2.2 mmol, 2.7 eq) in DMF (4 mL) at 25° C. were added EDCl-HCl (169 mg, 0.88 mmol, 1.1 eq) and HOBt (135 mg, 0.88 mmol, 1.1 eq). The resulting mixture was stirred at 25° C. for 20 h, and diluted with water. The mixture was extracted with DCM (4×30 mL), and concentrated. The crude product was purified by FCC using iPrOH/DCM (1/50, 1/25, 1/10) as eluant to afford a fairly pure product 3 (586 mg, 87%) as a white solid. Analysis of compound 3 by LCMS m/z: 846 (M+1), 848 (M+Na).

TFA (3 mL) was slowly added into a solution of 3 (502 mg, 0.59 mmol) and triethylsilane (300 µL) in DCM (9 mL) at 25° C. The resulting mixture was stirred at room temperature for 1 h, and concentrated. The residue was partitioned between DCM (90 mL) and 1 M $K_2CO_3$ (30 mL). The aqueous phase was extracted with DCM (4×40 mL). The combined organic layers were dried over $K_2CO_3$, and filtered. The filtrate was concentrated to provide a free amine 4 (429 mg, 97%). Analysis of compound 4 by LCMS m/z: 746 (M+1).

A mixture of the DISCO-PEG4-acid (102 mg, 0.16 mmol, 1 eq), HATU (80 mg, 0.20 mmol, 1.3 eq) and DIPEA (70 µL, 0.42 mmol, 2.6 eq) in DMF (2 mL) was stirred for 1 h. A solution of the amine 4 (120 mg, 0.16 mmol, 1 eq) in DMF (4 mL) was added into the above solution. The resulting mixture was stirred for 2 h, and concentrated to dryness. The residue was dissolved in EA/Hex (80 mL/20 mL), and washed with water. The crude product was purified by FCC ($NEt_3$/iPrOH/DCM=1/0/200, 1/15/200) to afford ester 5 (170 mg, 78%) as a white solid. Analysis of by LCMS m/z: 683.6 ([(M+2)/2].

The methyl ester 5 (134 mg, 0.10 mmol, 1 eq) was treated with LiOH—$H_2O$ (6.4 mg, 0.15 mmol) in THF/water (5 mL/1.7 mL) at 25° C. for 20 h. The mixture was concentrated to dryness. The crude product was purified by FCC ($NEt_3$/iPrOH/DCM=2/10/200, 2/20/200, 2/40/200) to afford lithium salt of DBCO-PEG-MMAF (105 mg, 77%) as a white solid. Analysis of DBCO-PEG-MMAF by LCMS m/z: 677 [(M+2)/2], 1352 (M+1), 1350 (M−1).

The trastuzumab variants were conjugated to an exemplary cytotoxic agent, MMAF, using a constrained cyclooctyne reagent. In brief, DBCO-MMAF (ACME Bioscience; Palo Alto, Calif.) was dissolved in DMSO to a final concentration of 5 mM. The compound was diluted with PBS to 1 mM and then added to the purified protein sample in IMAC elution buffer to final drug concentration of 100 µM. Mixture was incubated at RT (20° C.) for 17 hours. The reaction was stopped by adding sodium azide to final concentration of 100 mM and buffer exchanged using Zeba™ plates (Thermo Scientific, Waltham, Mass.) equilibrated in 1×PBS. Filtrate was then passed through a MUSTANG® Q plate (Pall Corp., Port Washington, N.Y.) to remove endotoxins.

E. Analysis of Antibody-Drug Conjugates.

Following conjugation, the antibody-drug conjugate samples were quantified on a Caliper GXII system (Perkin Elmer, Waltham, Mass.) by comparing to a series of mass standards of HERCEPTIN® run on the same Protein Express LabChip® (Caliper Life Sciences #760499). The samples were prepared for analysis as specified in the Protein Express Reagent Kit (Caliper Life Sciences

760328) with the exception that the samples (mixed in sample buffer+50 mM NEM) were heated at 65° C. for 10 minutes prior to analysis on the Caliper system. Drug conjugation did not cause any dissociation or aggregation of the intact IgG scaffold as determined by analytical size-exclusion chromatography.

These antibody drug conjugates were assayed for the degree of conjugation, or drug-to-antibody ratio (DAR) by mass spectrometry analysis of intact protein conjugates. DAR values were calculated as the weighted average of the deconvoluted mass spectrum peak intensities for each IgG drug-linker conjugate species DAR 0, 1, and 2). A high degree of conjugation was observed with DAR values from a low of 1.2 to a high of 1.9, e.g., from 1.48 to 1.70, that correlated well with the activity and specificity of the pAMFRS variant used to produce each respective ADC sample (FIG. 2A).

F. Cytoxicity of Antibody-Drug Conjugates.

The cell killing activity (cytotoxicity) of the conjugated ADC was measured using a cell-based proliferation assay. The Her2-positive breast cancer cell line SKBR3 was obtained from ATCC and maintained in DMEM/Nutrient F-12 Ham (50:50), high glucose (Cellgro-Mediatech; Manassas, Va.) supplemented with 10% heat-inactivated fetal bovine serum (Hyclone; Thermo Scientific; Waltham, Mass.), 2 mM glutamax (Invitrogen; Carlsbad, Calif.) and 1× Pencillin/streptomycin (Cellgro-Mediatech; Manassas, Va.). Adherent cells were washed twice with calcium and magnesium-free Phosphate Balanced Saline (PBS) and harvested with HYQ® SE™ (Hyclone; Thermo Scientific; Waltham, Mass.). A total of $1 \times 10^3$ or $3 \times 10^3$ cells in a volume of 40 ml were seeded in each well of a 96-well half area flat bottom white polystyrene plate. The cells were allowed to adhere overnight at 37° C. in a $CO_2$ incubator. ADC variants were formulated at 2× concentration in DMEM/F12, medium and filtered through sterile SpinX cellulose acetate filtered 2 ml centritube (Corning Costar, Cat#8160). 40 µl of filter-sterilized ADCs were added into treatment wells and plates were cultured at 37° C. in a $CO_2$ incubator for 120 hrs. For cell viability measurement. 80 µl of Cell Titer-Glo® reagent (Promega Corp. Madison, Wis.) was added into each well, and plates were processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response-variable slope, 4 parameter fit equation using GraphPad Prism® (GraphPad v 5.00, Software; San Diego, Calif.).

Compared to the unconjugated trastuzumab control, which is ineffective at cell killing at the concentrations tested, the trastuzumab-MMAF conjugates exhibited potent cytotoxicity with EC50 values ranging from 0.043 nM to 0.071 nM (FIG. 2B). These values are in good agreement with published EC50 values for trastuzumab-DM1. ADCs generated by random conjugation methods.

In summary, this example demonstrates that site-specific incorporation of pAMP facilitates near complete conjugation of a DBCO-PEG-monomethyl auristatin (DBCO-PEG-MMAF) drug to the tumor-specific, HER2-binding IgG (trastuzumab) using strain-promoted aside-alkyne cycloaddition (SPAAC) copper-free click chemistry. The resultant ADCs were highly potent at inducing cytotoxicity in in vitro cell assays. The method described herein can be used to produce homogeneous ADCs with drug-to-antibody ratio values approaching the theoretical limit of two drugs per antibody.

Example 3. Determine the High Fidelity of pAMF-Specific tRNA Synthetases in Cell Free Synthesis of Antibody-Drug Conjugates The high degree of amber codon suppression that was observed only in the presence of pAMF, the high ADC DAR value, and high drug potency mediated by pAMFRS variant B03 (FIG. 4A) all together indicated that this synthetase variant possessed a high degree of specificity for pAMF. The difference in DAR between the 6 Trastuzumab preps produced with the 6 different synthetases (FIGS. 4A and 4B) is most likely attributable to differences in the efficiency and specificity of pAMF incorporation. This is for several reasons: (1) the site of pAMF incorporation was the same, so positional effects that can lead to variable conjugation efficiency are not a factor; (2.) the conjugation reactions proceeded for 16 h, past the time point at which the ADC conjugation reaction has plateaued; and (3) the mass spectrometric method of DAR analysis offers very accurate and robust analysis, making inaccuracy of measurement highly unlikely, and (4) the observed DAR and $EC_{50}$ values correlate very well with the activity/specificity ratio ($GFP^{1\ mM\ pAMF}/GFP^{No\ pAMF}$) of the synthetase variant used to produce each ADC. It thus seems most likely that the lower DAR samples are the result of misincorporation events by lower fidelity synthetases, which lead to production of full-length HC species with natural amino acids at position 136 that cannot read with the DBCO drug linker. To follow up on pAMFRS incorporation fidelity, mass spectrometry analysis was used as a high resolution method to determine the precise fidelity of pAMFRS variant B03. Aminoacyl tRNA synthetase fidelity percentage can be defined as the frequency with which the enzyme charges its cognate tRNA, with its cognate amino acid versus any other amino acid. To derive this number, the frequency of pAMF incorporation versus any other amino acids at the position 136 TAG codon in the trastuzumab heavy chain was measured. Trastuzumab HC S136-TAG was coexpressed with trastuzumab light chain in the presence of pAMFRS variant B03, amber suppressor tRNA, and 1 mM pAMF in a 30 mL OCFS reaction. The full-length, assembled IgG was purified to >90% purity prior to tryptic digestion and mass spectrometry (MS) analysis of the pAMF-incorporated HC peptide. MS data were acquired first with an MS-only method, followed by a data-dependent MS/MS method with preferential selection for the target tryptic peptides containing pAMF, Phe, Tyr, or Gln at position 136. Phe, Tyr, and Gln misincorporation when using other amber suppression systems and as endogenous amber suppression events involving mismatch decoding of TAG codons by endogenous tRNAs was previously observed. The tandem MS of the trastuzumab HC-S136pAMF tryptic peptide positively identified the presence of pAMF at position 136. In addition, tryptic peptides containing Phe, Tyr, or Gln at HC position 136 and all other Phe positions in the protein could not be detected above the spectral noise level. Furthermore, no measurable nonsuppressed S136TAG truncation product in a parallel OCFS reaction containing $^{14}C$Leu, which indicates a high degree of pAMF incorporation was observed. Since no misincorporated peptides were observed, the maximum rate of misincorporation would be the noise level, or limit of detection of our MS method. Fidelity percentage was calculated as the ratio of the signal intensity for the pAMF-incorporated target peptide to the spectral noise intensity at the expected position of a Phe, Tyr, or GM-containing target peptide to yield a fidelity percentage of at least 99.8% for pAMF-RS variant B03 (Table 1).

TABLE 1

Phenylalanine-containing peptides found in the tryptic digest of trastuzumab HC-S136pAMF

| Chain | Phe Position | Amino Acid Sequence | SEQ ID NO | Fidelity |
|---|---|---|---|---|
| HC | 136 | ST-pAMF-GGTAALGCLVK | SEQ ID NO: 4 | 99.8 |
| LC | 53 | LLIYSASFLYSGVPSR | SEQ ID NO: 5 | 99.8 |
| LC | 116, 118 | RTVAAPSVFIFPPSDEQLK | SEQ ID NO: 6 | 99.8 |
| HC | 67 | FTISADTSK | SEQ ID NO: 7 | 99.1 |
| HC | 27 | LSCAASGFNIK | SEQ ID NO: 8 | 99.7 |
| HC | 275 | FNWYVDGVEVHNAK | SEQ ID NO: 9 | 99.6 |
| HC | 404, 405 | TTPPVLDSDGSFFLYSK | SEQ ID NO: 10 | 99.7 |
| HC | 372 | GFYPSDIAVEWESNGQPENNYK | SEQ ID NO: 11 | 99.7 |
| HC | 67 | GRFTISADTSK | SEQ ID NO: 12 | 99.9 |

A small amount of full-length trastuzumab synthesized in the absence of pAMF-RS was observed, presumably due to amber suppression events attributable to mismatch decoding of the TAG codon by endogenous tyrosine and glutamine-charged tRNAs (TAT/TAC, and CAG-decoding tRNAs, respectively). However, these misincorporation events were not observed on our LC-MS/MS-based peptide analysis. This suggests that such endogenous amber suppression events occur very rarely, if at all, in the presence of the highly efficient pAMF-based amber suppression system described herein.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition comprising an aminoacyl-tRNA synthetase (RS) wherein the RS:
   i) preferentially aminoacylates to a degree of greater than 90% a tRNA with para-methylazido-L-phenylalanine (pAMF) compared to the 20 common naturally occurring amino acids;
   ii) has a sequence identity of over 90% to *Methanococcus jannaschii* tyrosyl tRNA synthetase (TyrRS) having SEQ ID NO:1; and
   iii) using SEQ ID NO: 1 as a reference sequence, has:
      a) at position L65 amino acid: A or V;
      b) at position F108 amino acid: Y or W;
      c) at position D158 amino acid: A;
      d) at position Y32 amino acid: T or V or A; and
      e) at position I159 amino acid: S or G or V.

2. The composition of claim 1, having an amino acid substitution at position Q109 selected from the group of amino acids consisting of L or M or I.

3. The composition of claim 1, wherein the RS has a sequence identity of at least 90% of SEQ ID NO:1 and has amino acid substitutions selected from the group consisting of:
   i) Y32T, L65A, F108Y, Q109L and I159S;
   ii) Y32V, L65A, F108W, Q109M and I159G;
   iii) Y32A, L65V, F108W and I159G;
   iv) Y32V, L65V, F108Y and I159V;
   v) Y32T, L65V, F108W and I159S; and
   vi) Y32V, L65V, F108W, G109I and I159S.

4. The composition of claim 1, wherein the RS using SEQ ID NO:1 as a reference sequence, has
   a) at position L65 amino acid: V;
   b) at position F108 amino acid: W;
   c) at position D158 amino acid: A;
   d) at position Y32 amino acid: A; and
   e) at position I159 amino acid: G.

5. A polynucleotide encoding an aminoacyl-tRNA synthetase (RS) wherein the RS:
   i) preferentially aminoacylates to a degree of greater than 90% a tRNA with para-methylazido-L-phenylalanine (pAMF) compared to the 20 common naturally occurring amino acids;
   ii) has a sequence identity of over 90% to *Methanococcus jannaschii* tyrosyl tRNA synthetase (TyrRS) having SEQ ID NO: 1; and
   iii) using SEQ ID NO: 1 as a reference sequence, has:
      a) at position L65 amino acid: A or V;
      b) at position F108 amino acid: Y or W;
      c) at position D158 amino acid: A;
      d) at position Y32 amino acid: T or V or A; and
      e) at position I159 amino acid: S or G or V.

6. The polynucleotide of claim 5, having an amino acid substitution at position Q109 selected from the group of amino acids consisting of L or M or I.

7. The polynucleotide of claim 5, wherein the RS has a sequence identity of at least 90% of SEQ ID NO: 1 and has amino acid substitutions selected from the group consisting of:
   i) Y32T, L65A, F108Y, Q109L and I159S;
   ii) Y32V, L65A, F108W, Q109M and I159G;
   iii) Y32A, L65V, F108W and I159G;
   iv) Y32V, L65V, F108Y and I159V;
   v) Y32T, L65V, F108W and I159S; and
   vi) Y32V, L65V, F108W, G109I and I159S.

8. The polynucleotide of claim 5, wherein the RS using SEQ ID NO:1 as a reference sequence, has
   a) at position L65 amino acid: V;
   b) at position F108 amino acid: W;
   c) at position D158 amino acid: A;
   d) at position Y32 amino acid: A; and
   e) at position I159 amino acid: G.

9. A cell free protein synthesis system for selectively incorporating para-methylazido-L-phenylalanine (pAMF) into a protein of interest, the system comprising:
   a) a cell free extract of bacteria having biologically functioning tRNA, amino acids and ribosomes necessary for cell free protein synthesis;
   b) a polynucleotide having a coding region encoding the protein of interest and including a suppression codon selectively positioned within its coding region;
   c) methylazido-L-phenylalanine in a concentration sufficient to permit selective incorporation of pAMF into the protein of interest;
   d) a tRNA able to be charged with pAMF and complementary to the suppression codon of the protein of interest; and
   e) an aminoacyl-tRNA synthetase (RS) wherein the RS:
      i) preferentially aminoacylates to a degree of greater than 90% a tRNA with pAMF compared to the 20 common naturally occurring amino acids;
      ii) has a sequence identity of over 90% to *Methanococcus jannaschii* tyrosyl tRNA synthetase (TyrRS) having SEQ ID NO:1; and
      iii) using SEQ ID NO:1 as a reference sequence, has:
         a) at position L65 amino acid: A or V;
         b) at position F108 amino acid: Y or W;
         c) at position D158 amino acid: A;
         d) at position Y32 amino acid: T or V or A; and
         e) at position I159 amino acid: S or G or V.

10. The cell free protein synthesis system of claim 9, wherein the RS has an amino acid substitution at position Q109 selected from the group of amino acids consisting of L or M or I.

11. The cell free protein synthesis system of claim 9, wherein the RS has a sequence identity of at least 90% of SEQ ID NO: 1 and has amino acid substitutions selected from the group consisting of:

i) Y32T, L65A, F108Y, Q109L and I159S;
ii) Y32V, L65A, F108W, Q109M and I159G;
iii) Y32A, L65V, F108W and I159G;
iv) Y32V, L65V, F108Y and I159V;
v) Y32T, L65V, F108W and I159S; and
vi) Y32V, L65V, F108W, G109I and I159S.

12. The cell free protein synthesis system of claim 9, wherein the RS using SEQ ID NO:1 as a reference sequence, has
    a) at position L65 amino acid: V;
    b) at position F108 amino acid: W;
    c) at position D158 amino acid: A;
    d) at position Y32 amino acid: A; and
    e) at position I159 amino acid: G.

13. The cell free protein synthesis system of claim 9, wherein the cell free extract has an active oxidative phosphorylation system.

14. The cell free protein synthesis system of claim 9, wherein the protein of interest is an antibody or antibody fragment.

15. A method for selectively incorporating para-methylazido-L-phenylalanine (pAMF) into a protein of interest, the method comprising the steps of:
    a) combining a cell free extract of bacteria having containing biologically functioning tRNA, amino acids and ribosomes necessary for cell free protein synthesis with the following reagents:
        i) a polynucleotide having a coding region encoding the protein of interest and including a suppression codon selectively positioned within its coding region;
        ii) methylazido-L-phenylalanine in a concentration sufficient to permit selective incorporation of pAMF into the protein of interest;
        iii) a tRNA able to be charged with pAMF and complementary to the suppression codon of the protein of interest; and
        iv) an aminoacyl-tRNA synthetase (RS) wherein the RS:
            preferentially aminoacylates to a degree of greater than 90%, a tRNA with pAMF compared to the 20 common naturally occurring amino acids;
            has a sequence identity of over 90% to *Methanococcus jannaschii* tyrosyl tRNA synthetase (TyrRS) having SEQ ID NO: 1; and
            using SEQ ID NO: 1 as a reference sequence, has:
                a) at position L65 amino acid: A or V;
                b) at position F108 amino acid: Y or W;
                c) at position D158 amino acid: A;
                d) at position Y32 amino acid: T or V or A; and
                e) at position I159 amino acid: S or G or V; and
    b) incubating the combination of step (a) under conditions permitting selective incorporation of pAMF into the protein of interest.

16. The method of claim 15, wherein the RS further has an amino acid substitution at position Q109 selected from the group of amino acids consisting of L or M or I.

17. The method of claim 15, wherein the RS has sequence identity of at least 90% of SEQ ID NO:1 and further has an amino acid substitution selected from the group of substitutions consisting of:
    i) Y32T, L65A, F108Y, Q109L, and I159S;
    ii) Y32V, L65A, F108W, Q109M, and I159G;
    iii) Y32A, L65V, F108W, and I159G;
    iv) Y32V, L65V, F108Y, and I159V;
    v) Y32T, L65V, F108W, and I159S; and
    vi) Y32V, L65V, F108W, G109I, and I159S.

18. The method of claim 15, wherein the RS using SEQ ID NO:1 as a reference sequence, has
    a) at position L65 amino acid: V;
    b) at position F108 amino acid: W;
    c) at position D158 amino acid: A;
    d) at position Y32 amino acid: A; and
    e) at position I159 amino acid: G.

19. The method of claim 15, wherein the cell free extract has an active oxidative phosphorylation system.

20. The method of claim 15, wherein the protein of interest is an antibody or antibody fragment.

21. The method of claim 15, further comprising conjugating a biologically active adduct to the pAMF of the protein of interest.

22. The method of claim 21, wherein the conjugation is by a 1,3-cycloaddition of an azide with a strained alkyne.

* * * * *

SEQUENCE LISTING

```
<160> NUMBER OF SEQ ID NOS: 12

<210> SEQ ID NO 1
<211> LENGTH: 306
<212> TYPE: PRT
<213> ORGANISM: Methanococcus jannaschii
<220> FEATURE:
<223> OTHER INFORMATION: wild-type (WT) tyrosyl tRNA synthetase (TyrRS),
      reference sequence

<400> SEQUENCE: 1

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125
```

```
Arg Ala Arg Arg Ser Met Glu Leu Ile Ala Arg Glu Asp Glu Asn Pro
            130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 2
<211> LENGTH: 306
<212> TYPE: PRT
<213> ORGANISM: Artificial Sequence
<220> FEATURE:
<223> OTHER INFORMATION: aminoacyl-tRNA synthetase (RS) variant

<400> SEQUENCE: 2

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Gly His
145                 150                 155                 160

Tyr Leu Gly Val Asp Val Ala Val Gly Gly Met Glu Gln Arg Lys Ile
                165                 170                 175
```

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 3
<211> LENGTH: 306
<212> TYPE: PRT
<213> ORGANISM: Artificial Sequence
<220> FEATURE:
<223> OTHER INFORMATION: aminoacyl-tRNA synthetase (RS) variant

<400> SEQUENCE: 3

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 4
<211> LENGTH: 14
<212> TYPE: PRT
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine
<220> FEATURE:
<221> NAME/KEY: MOD_RES
<222> LOCATION: (3)...(3)
<223> OTHER INFORMATION: Xaa = para-methylazido-L-phenylalanine (pAMF)

<400> SEQUENCE: 4

Ser Thr Xaa Gly Gly Thr Ala Ala Leu Gly Cys Leu Val Lys
1               5                   10

<210> SEQ ID NO 5
<211> LENGTH: 15
<212> TYPE: PRT
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 5

Leu Leu Ile Tyr Ser Ala Ser Phe Leu Tyr Gly Val Pro Ser Arg
1               5                   10                  15

<210> SEQ ID NO 6
<211> LENGTH: 19
<212> TYPE: PRT
<213> ORGANISM: Artificial Sequence
<220> FEATURE:
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 6

Arg Thr Val Ala Ala Pro Ser Val Phe Ile Phe Pro Pro Ser Asp Glu
1               5                   10                  15

Gln Leu Lys

<210> SEQ ID NO 7
<211> LENGTH: 9
<212> TYPE: PRT
<213> ORGANISM: Artificial Sequence
```

```
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 7

Phe Thr Ile Ser Ala Asp Thr Ser Lys
 1               5

<210> SEQ ID NO 8
<211> LENGTH: 11
<212> TYPE: PRT
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 8

Leu Ser Cys Ala Ala Ser Gly Phe Asn Ile Lys
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 9

Phe Asn Trp Tyr Val Asp Gly Val Glu Val His Asn Ala Lys
 1               5                  10

<210> SEQ ID NO 10
<211> LENGTH: 17
<212> TYPE: PRT
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 10

Thr Thr Pro Pro Val Leu Asp Ser Asp Gly Ser Phe Phe Leu Tyr Ser
 1               5                  10                  15

Lys

<210> SEQ ID NO 11
<211> LENGTH: 22
<212> TYPE: PRT
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 11

Gly Phe Tyr Pro Ser Asp Ile Ala Val Glu Trp Glu Ser Asn Gly Gln
 1               5                  10                  15

Pro Glu Asn Asn Tyr Lys
                20

<210> SEQ ID NO 12
<211> LENGTH: 11
<212> TYPE: PRT
```

```
<213> ORGANISM: Artificial Sequence
<220> FEATURE:
<223> OTHER INFORMATION: synthetic Her2-specific monoclonal antibody
      trastuzumab HC-S136pAMF tryptic digest peptide containing
      phenylalanine

<400> SEQUENCE: 12

Gly Arg Phe Thr Ile Ser Ala Asp Thr Ser Lys
 1               5                  10
```